(12) United States Patent
Neuschäfer et al.

(10) Patent No.: US 6,289,144 B1
(45) Date of Patent: *Sep. 11, 2001

(54) SENSOR PLATFORM AND METHOD FOR THE PARALLEL DETECTION OF A PLURALITY OF ANALYTES USING EVANESCENTLY EXCITED LUMINESCENCE

(75) Inventors: Dieter Neuschäfer, Muttenz (CH); Gert Ludwig Duveneck, Bad Krozingen (GB); Michael Pawlak, Laufenberg (GB); Uwe Pieles, Schliengen (GB); Wolfgang Budach, Marly (CH)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/487,560

(22) Filed: Jan. 19, 2000

Related U.S. Application Data

(63) Continuation of application No. 08/945,588, filed as application No. PCT/EP96/01817 on May 2, 1996, now Pat. No. 6,078,705.

(30) Foreign Application Priority Data

May 12, 1995 (CH) .................................... 1396/95

(51) Int. Cl.[7] ...................................................... G02B 6/00
(52) U.S. Cl. ............................ 385/12; 385/37; 422/82.11
(58) Field of Search ....................... 385/12, 37, 129–132, 385/4, 8, 14, 31; 422/82.11

(56) References Cited

U.S. PATENT DOCUMENTS

| 5,081,012 | 1/1992 | Flanagan et al. | 435/7.9 |
| 5,082,629 | 1/1992 | Burgess, Jr. et al. | 385/12 |
| 5,163,118 | 11/1992 | Lorenzo et al. | 385/132 |
| 5,512,492 | * 4/1996 | Herron et al. | 436/518 |
| 5,822,472 | 10/1998 | Danielzik et al. | 385/12 |

FOREIGN PATENT DOCUMENTS

| 91/10122 | 7/1991 | (WO) . |
| 92/14177 | 8/1992 | (WO) . |
| 95/03538 | 2/1995 | (WO) . |

OTHER PUBLICATIONS

M. Gale, et al., Optical Engineering, vol. 34, No. 8, 1995, pp. 2396–2406.

R. Sutherland, et al., Clinical Chemistry, vol. 30, No. 9, 1984, pp. 1533–1538.

* cited by examiner

Primary Examiner—Rodney Bovernick
Assistant Examiner—Ellen Kim
(74) Attorney, Agent, or Firm—Wenderoth, Lind & Ponack, L.L.P.

(57) ABSTRACT

The invention relates to a sensor platform based on at least two planar, separate, inorganic dielectric waveguiding regions on a common substrate and to a method for the parallel evanescent excitation and detection of the luminescence of identical or different analytes. The invention relates also to a modified sensor platform that consists of the sensor platform having the planar, separate, inorganic dielectric waveguiding regions and one or more organic phases immobilised thereon. A further subject of the invention is the use of the sensor platform or of the modified sensor platform in a luminescence detection method for quantitative affinity sensing and for the selective quantitative determination of luminescent constituents of optically opaque solutions.

34 Claims, 6 Drawing Sheets

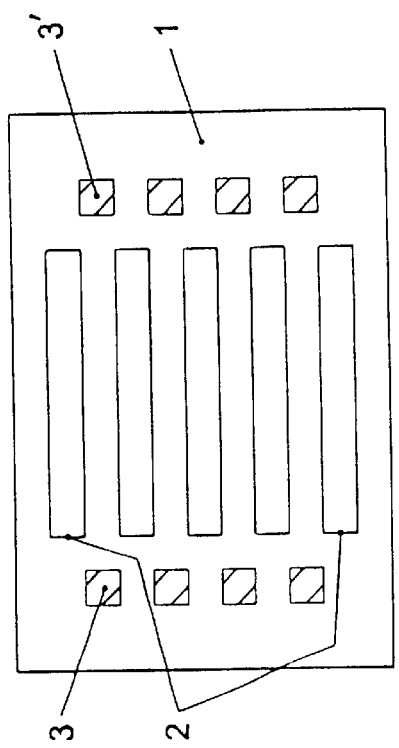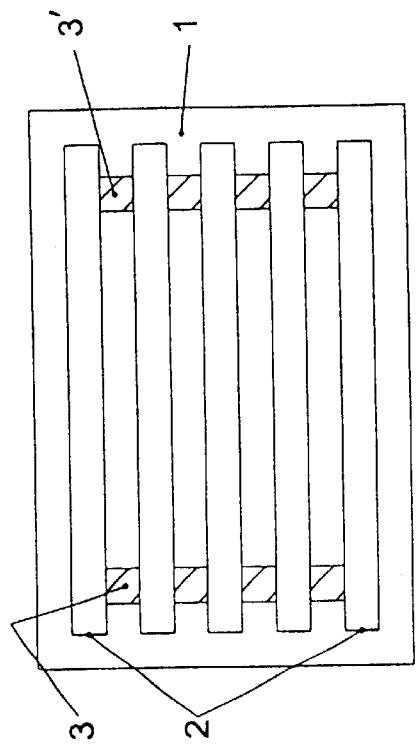
FIGURE 2B
FIGURE 2D
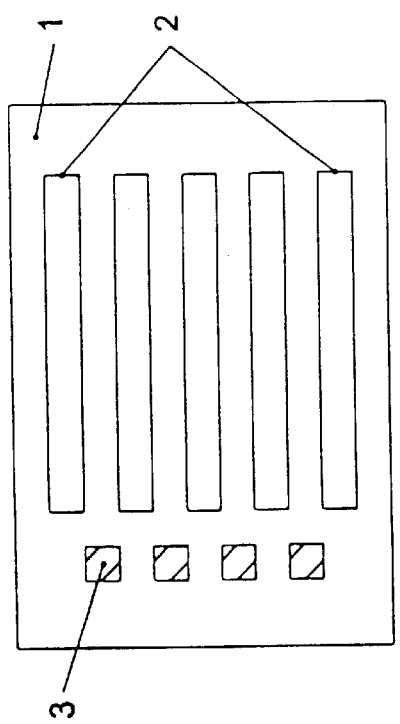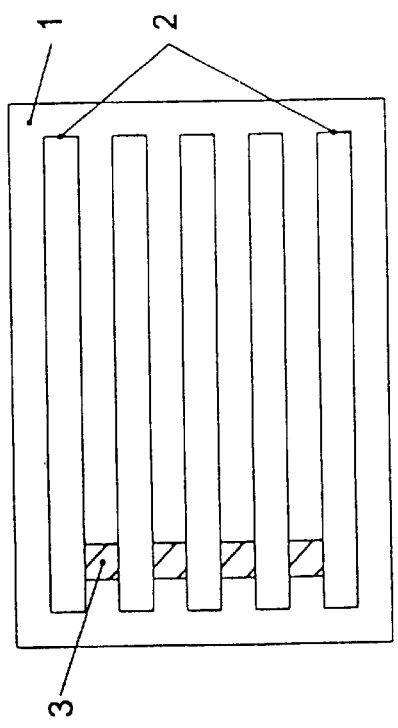
FIGURE 2A
FIGURE 2C

SENSOR PLATFORM AND METHOD FOR THE PARALLEL DETECTION OF A PLURALITY OF ANALYTES USING EVANESCENTLY EXCITED LUMINESCENCE

This is a continuation of Ser. No. 08/945,588, Oct. 28, 1997, now U.S. Pat. No. 6,078,705, which is a 371 of PCT/EP96/01817, May 2, 1996.

The invention relates to a sensor platform based on at least two planar, separate, inorganic dielectric waveguiding regions on a common substrate and to a method for the parallel evanescent excitation and detection of the luminescence of identical or different analytes. The invention relates also to a modified sensor platform that consists of the sensor platform having the planar, separate, inorganic dielectric waveguiding regions and one or more organic phases immobilised thereon. A further subject of the invention is the use of the sensor platform or of the modified sensor platform in a luminescence detection method for quantitative affinity sensing and for the selective quantitative determination of luminescent constituents of optically opaque solutions.

If a lightwave is coupled into a planar waveguide that is surrounded by media of a lower refractive index, it is confined by total reflection at the boundaries of the waveguiding layer. In the simplest case, a planar waveguide consists of a three-layer system: substrate, wave-guiding layer, superstrate (or sample to be investigated), the waveguiding layer having the highest refractive index. Additional intermediate layers can further improve the action of the planar waveguide.

In that arrangement, a fraction of the electromagnetic energy enters the media of lower refractive index. That portion is termed the evanescent (=decaying) field. The strength of the evanescent field depends to a very great extent upon the thickness of the waveguiding layer itself and upon the ratio of the refractive indices of the waveguiding layer and of the media surrounding it. In the case of thin waveguides, i.e. layer thicknesses that are the same as or smaller than the wavelength that is to be guided, discrete modes of the guided light can be distinguished.

Using an evanescent field, it is possible, for example, to excite luminescence in media of relatively low refractive index, and to excite that luminescence in the immediate vicinity of the waveguiding region only. That principle is known as evanescent luminescence excitation.

Evanescent luminescence excitation is of great interest in the field of analysis, since the excitation is limited to the immediate vicinity of the waveguiding layer. Methods and apparatus for determining the evanescently excited luminescence of antibodies or antigens labelled with luminescent dyes are known and are described, for example, in U.S. Pat. No. 4,582,809. The arrangement claimed therein uses an optical fibre for evanescent luminescence excitation. Such optical fibres have, typically, a diameter of up to a millimeter and guide a large number of modes when laser light is coupled into them. The evanescently excited luminescence can be measured easily only by means of the portion coupled back into the fibres. A further disadvantage is that the apparatus is relatively large and comparatively large volumes of sample are required. There is little scope for any further substantial reduction in the size of the arrangement, let alone for miniaturising it to produce integrated optical sensors.

Any increase in sensitivity is generally associated with an increase in the size of the arrangement.

Photometric instruments for determining the luminescence of biosensors under evanescent excitation conditions using planar optical waveguides are likewise known and are described, for example, in WO 90/06503. The waveguiding layers used in that specification are from 160 nm to 1000 nm thick and the excitation wave is coupled in without grating couplers.

Various attempts have been made to increase the sensitivity of evanescently excited luminescence and to produce integrated optical sensors. For example, a report in Biosensors & Bioelectronics 6 (1991), 595–607, describes planar monomodal or low-modal waveguides that are produced in a two-step ion-exchange process and in which the excitation wave is coupled in using prisms. The affinity system used is human immunoglobulin G/fluorescein-labelled protein A, the antibody being immobilised on the waveguide and the fluorescein-labelled protein A to be detected being added in phosphate buffer to a film of polyvinyl alcohol with which the measuring region of the waveguide is covered.

A considerable disadvantage of that method is that only small differences in refractive index between the waveguiding layer and the substrate layer can be achieved, with the result that the sensitivity is relatively low.

The sensitivity is given as 20 nM of fluorescein-labelled protein A. That is still not satisfactory for the determination of very small traces and a further increase in sensitivity is therefore required. In addition, the coupling-in of light using prisms is difficult to reproduce and to carry out in practice owing to the great extent to which the coupling-in efficiency is dependent upon the quality and size of the contact surface between the prism and the waveguide.

In U.S. Pat. No. 5,081,012 a different principle is proposed. The planar waveguiding layer is from 200 nm to 1000 nm thick and contains two gratings, one of which is in the form of a reflection grating, with the result that the coupled-in lightwave has to pass at least twice through the sensor region between the gratings. That is supposed to produce increased sensitivity. A disadvantage is that the reflected radiation can lead to an undesirable increase in background radiation intensity.

WO 91/10122 describes a thin-layered spectroscopic sensor which comprises a coupling-in grating and a physically remote coupling-out grating. It is suitable especially for absorption measurement if an inorganic metal oxide of high refractive index is used as the waveguiding layer. Various embodiments that are suitable for the coupling-in and coupling-out of multi-chromatic light sources are described. The preferred thickness of the waveguiding layer is greater than 200 nm and the grating depth should be approx. 100 nm. Those conditions are not suitable for luminescence measurements in affinity sensing since only low sensitivity is obtained. That is confirmed in Appl. Optics Vol. 29, No. 31 (1990), 4583–4589 by the data for the overall efficiency of those systems: 0.3% at 633 nm and 0.01% at 514 nm.

In another embodiment of the same sensor, a plurality of polymeric planar waveguiding layers that can be used as a gas-mixture analyser are applied to a substrate. Use is made in that case of the change in the effective refractive index or the change in the layer thickness of the polymer waveguide on contact with, for example, solvent vapours. The waveguiding structure is physically altered thereby. However, such changes are totally unsuitable for luminescence measurements in affinity sensing since the coupling-in is altered, increasing scatter occurs and there can be a significant decrease in sensitivity.

The production of planar waveguides is a process in which the planarity of the substrate, the constant thickness and homogeneity of the waveguiding layer and the refractive index of the material used therefor are of extreme importance. That is described, for example, in EP-A-0 533 074, and that specification proposes the application of inorganic waveguides to plastics substrates. That offers the advantage that, for example, the structuring of the grating coupler can be effected in an economical manner by impressing the structure into the plastics. On the other hand, however, the requirements with regard to the optical quality of the plastics substrates are also high.

Planar waveguides offer considerable advantages for industrial production over waveguides based on fibre optics. In particular, it is generally necessary in the case of fibres to polish the cut ends in order to achieve perfect optical quality. Planar waveguides, on the other hand, can be produced in sheet form and then stamped, broken or cut to the desired size. Finishing of the edges is unnecessary in most cases, making mass production more economical.

Further advantages of planar waveguides having grating couplers are simple adjustment in the measuring apparatus or in the measuring arrangement and simple application of a coating, for example for the immobilisation of an analyte. Standard processes from coating technology that allow the production of reproducible, constant layer thicknesses can be used for that purpose. Examples are spraying, knife application, spin-coating and dipping. Quality control can also be carried out in a simple manner using known, very precise methods. There are suitable, for example, microscopic or interferometric methods, ellipsometry or contact-angle measurements. Those methods cannot be used, or can be used only with difficulty, for curved surfaces, such as those found in waveguides based on fibre optics.

Along with the waveguiding layer itself, the nature of the coupling of the lightwave into the waveguiding layer represents a major problem. The requirements for gratings for coupling light into tapering waveguides for integrated optical sensors are indicated, for example, in Chemical, Biochemical and Environmental Fiber Sensors V, Proc. SPIE, Vol 2068, 313–325, 1994. The modulation depth of the grating and the layer thickness of the waveguide are described as critical features. The systems proposed in that publication can be used, for example, as integrated optical luminous indicators, although no reference is made to any luminescence to be detected.

If such planar waveguides having integrated grating couplers are to be used to measure luminescence, the features essential to their usefulness and to the achievement of a high degree of sensitivity are adequate coupling-in efficiency, as strong an evanescent field as possible and low attenuation of the guided wave. Those features are critically determined by the combination of refractive index of the waveguiding layer and of the substrate and of any intermediate layers, layer thickness of the waveguide, and structure, modulation depth and grating period of the grating coupler. Added to this, there are the requisite optical quality of the surfaces and the planarity or the roughness thereof.

A disadvantage of all the methods for the detection of evanescently excited luminescence described in the prior art is that only one sample at a time can be analysed on the sensor platform in the form of homogeneous film. In order to be able to carry out further measurements on the same sensor platform, laborious washing and cleaning steps are necessary. That is the case especially when an analyte that is different from the analyte of the first measurement is to be detected. In the case of an immunoassay, that generally means that the entire immobilised layer on the sensor platform has to be replaced or that a new sensor platform has to be used.

There is therefore a need for a method to be developed that allows a plurality of samples to be analysed in parallel, that is to say simultaneously or one immediately after another without additional cleaning steps.

WO 95/03538 proposes, for example, arranging above a continuous waveguiding layer a plurality of sample cells in the form of wells in a sample plate on top of the waveguiding layer. Under each sample cell is a grating that couples out a portion of the light guided through the waveguiding layer. The detection of the analytes is based on the change in the coupling-out angle as a function of the analyte concentration. Methods based on changes in refractive index are generally distinctly less sensitive than are luminescence methods.

WO 94/27137 proposes, for example, an apparatus and a method for carrying out immunoassays using evanescently excited fluorescence. The apparatus consists of a continuous optical waveguide having two plane-parallel surfaces and a lateral edge that acts in conjunction with a lens as coupling-in element. A plurality of specific binding partners are immobilised on at least one surface. In a preferred embodiment, those specific binding partners are arranged on the continuous waveguide so that they are physically separate from one another. In the working Example they are distributed in the form of dots over the surface of the waveguide.

On the basis of the embodiments disclosed, it must be assumed that the efficiency achieved by coupling-in via the lateral edge is lower than in the case of coupling-in via gratings; furthermore, owing to the large layer thickness (self-supporting waveguide) the strength of the evanescent field and hence the excitation efficiency is considerably lower than in the case of monomodal waveguides of relatively small layer thickness. Overall, the sensitivity of the arrangement is limited as a result.

Those arrangements in which various specific binding partners are applied to a continuous waveguiding layer also have the disadvantage that the excitation light excites all of the fluorophore-labelled molecules. Selection of measurement sites according to location is thus not possible. In addition, evanescently backcoupled fluorescence photons may contribute to the signal from the neighbouring dot and thus lead to measurement errors.

In integrated optics for applications in telecommunications, glass-based planar optical components are known that contain waveguides in the form of channels, the waveguiding channels being produced by the exchange of individual ions at the surface with the aid of masks (Glastechnische Berichte Vol. 62, page 285, 1989). A physically interconnected layer results which exhibits a slight increase in refractive index in the channels that have been doped with ions. The increase is generally less than 5%. Such components are complicated and expensive to produce.

In SPIE Vol 1587 Chemical, Biochemical and Environmental Fiber Sensors III (1991), pages 98–113, R. E. Kunz describes optical waveguides that fork and then come together again and that are suitable especially for integrated optical instruments, such as interferometers. Such structures are not suitable for evanescently excited luminescence measurement since the elements cannot be addressed individually and since the arrangement of a plurality of forks one after the other rapidly leads to large intensity losses for the lightwave coupled-in at the first fork. Since the opening angle of such forks is small (3° is typical), the distances between the two branches of a fork in the case of small components are short or else the dimensions of the components have to be made correspondingly larger, which is generally undesirable. In addition, the fixed phase relationship between the forked waves is not required for luminescence measurements.

In WO 92/19976, R. Kunz again describes an arrangement comprising a plurality of integrated measuring strips for detecting a complex signal; this may be, especially, the detection of an odour by an artificial nose.

The use of substantially monomodal, planar inorganic waveguides for luminescence detection methods is mentioned only generically in the prior art, without any description of the specific requirements associated with luminescence excitation and detection. In particular, there is no indication of the ranges of layer thickness or the depths of modulation with which good or very good results can be obtained.

It has now been found that it is possible to produce in a simple manner a sensor platform based on at least two planar, separate, inorganic, dielectric waveguiding regions on a common substrate, which platform is suitable for the parallel evanescent excitation and detection of the luminescence of identical or different analytes. Those separate waveguiding regions may each have one or more coupling gratings.

A substantial advantage of that sensor platform is that, for example, several sample solutions can be analysed simultaneously with a high degree of sensitivity. No washing or cleaning steps between individual measurements are required, with the result that a high sample throughput per unit of time is achieved. That is of great significance especially for routine analysis or in the field of genetic engineering analysis.

In addition to the analysis of a plurality of sample solutions simultaneously, it is also possible for one sample solution to be tested for several of its analytes simultaneously or in succession on one sensor platform. That is advantageous especially in the case of blood or serum testing which can thus be carried out especially quickly and economically.

When several sample solutions are analysed simultaneously, the separate waveguiding regions prevent cross-talk between luminescence signals from different samples. A high degree of selectivity and low error rates are achieved with this method.

The separation of the waveguiding regions also makes it possible to increase the selectivity and sensitivity still further by the targeted use of light sources of different wavelengths.

A further advantage of the sensor platform is that the individual separate waveguiding regions can be selectively addressed optically, chemically or fluidically.

Especially suitable is a sensor platform having physically or optically separate planar wave-guiding regions in which only one mode or a small number of modes are guided. It is distinguished by an especially high degree of sensitivity and an extremely small structure. As a rule, that degree of sensitivity is not achieved with multimodal waveguides of planar construction.

The excitation light can be coupled in, for example, using lenses, prisms or gratings or directly into the end face of the waveguiding layer.

The coupling-in and, where appropriate, coupling-out using gratings is generally simpler and more efficient than with lenses or prisms, with the result that the intensity of the coupled-in lightwave is likewise greater; this, in conjunction with a low degree of attenuation of the guided lightwave, contributes to the very high sensitivity of this arrangement.

The sensitivity can be increased still further by using as strong an evanescent field as possible. That offers the possibility of determining even very small amounts of luminescent material on the surface of the waveguiding layer.

A subject of the invention is a sensor platform consisting of a continuous transparent substrate and a transparent, planar, inorganic, dielectric waveguiding layer, wherein a) the transparent, inorganic, dielectric waveguiding layer is divided at least in the measuring region into at least two waveguiding regions by virtue of the fact that the effective refractive index in the regions in which the wave is guided is greater than in the surrounding regions or the division in the waveguiding layer is formed by a material on its surface that absorbs the coupled-in light;

b) the waveguiding regions are provided with one coupling-in grating each or with a common coupling-in grating in such a manner that the direction of propagation of the wave vector is maintained after the coupling-in, and c) where appropriate, the waveguiding regions are provided with one coupling-out grating each or with a common coupling-out grating.

The invention does not include arrangements of two waveguiding regions that, for example, initially branch in the form of a Y and are then joined together again at both ends, since in that case the direction of propagation of the wave vector changes after coupling-in. Such arrangements are already known and are used, for example, as interferometers.

In the present invention, the purpose of the separate waveguiding regions is to provide a sensor platform for the simultaneous detection of evanescently excited luminescence from one or more analytes.

The expressions "measuring section" and "measuring region" are used synonymously within the context of the present invention.

The geometric form of the separate waveguiding regions is in itself optional. It is advantageously governed by the structure of the apparatus as a whole in which the sensor platform is installed. Examples of geometric forms are lines, strips, rectangles, circles, ellipses, chess-board patterns, lozenges, honeycomb patterns or irregular mosaics. The divisions between the individual waveguiding regions are essentially straight lines. They can, for example, come to a point at the ends and they can be broader or narrower overall than is the measuring region.

The waveguiding regions are preferably arranged in the form of separate strips, rectangles, circles, ellipses and chessboard patterns.

The waveguiding regions are arranged especially in the form of parallel strips.

A further preferred embodiment is obtained when the waveguiding regions are arranged in the form of parallel strips that are joined together at one or both ends, with the direction of propagation of the wave vector remaining unchanged after the coupling-in.

Another advantageous embodiment is one in which the strips are joined together at one end and the other end is open, with the direction of propagation of the wave vector remaining unchanged /after the coupling-in.

BRIEF DESCRIPTION OF THE DRAWINGS

FIGS. 2a–2d show different embodiments of the present invention in which the coupling gratings are continuous;

FIG. 1a to 1d and 2a to 2d illustrate several more possible arrangements.

Figure 1A:
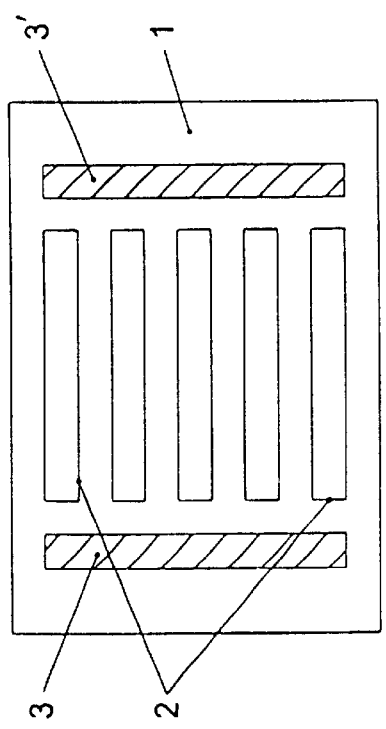
FIGS. 1a–1d show different embodiments of the present invention in which the coupling gratings are continuous.

The reference numerals denote:

1 the waveguiding layer which has been applied to a substrate;

2 the divisions, which are formed either by an absorbing material on the surface of the waveguiding layer or by a reduction in the effective refractive index in the plane of the layer, which in the simplest case is achieved by means of an air gap in place of the waveguiding layer;

3, 3' the coupling-in and coupling-out gratings, respectively.

In FIG. 1a, the waveguiding regions (=measuring regions) are interrupted by dividing regions. Those dividing regions do not come into contact with the coupling element.

Figure 1B:
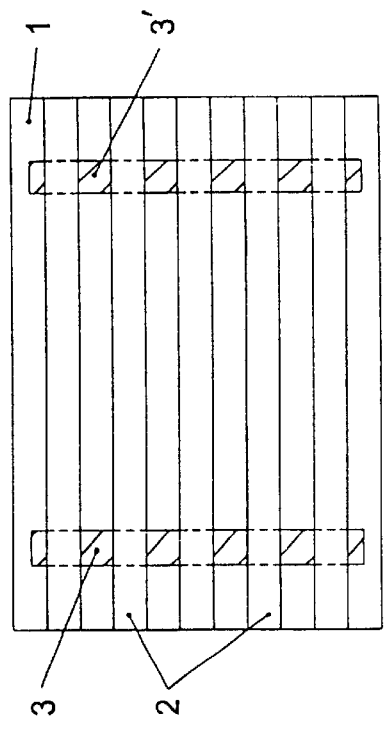

In the case of FIG. 1b, coupling-in and coupling-out gratings that are common to all measuring regions are present. There is no contact with the dividing regions.

Figure 1C:
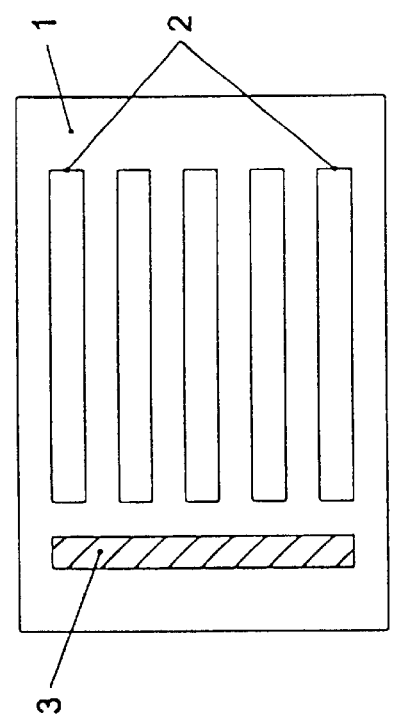

In FIG. 1c, the dividing regions extend beyond the coupling element. However, that does not affect the coupling-in in the waveguiding regions.

Figure 1D:
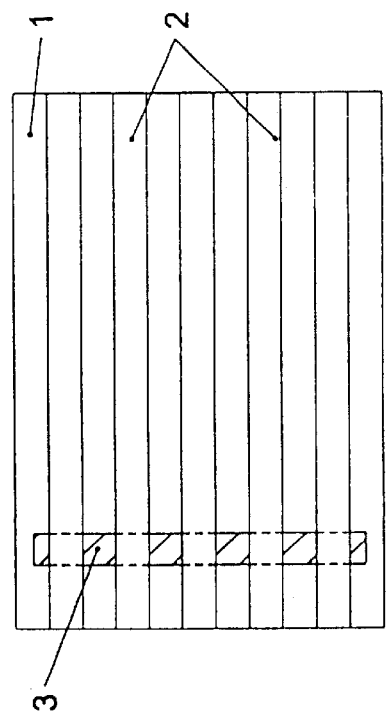

FIG. 1d comprises two coupling gratings but otherwise corresponds to FIG. 1c.

FIGS. 2a to 2d show an arrangement in which the coupling gratings are not continuous, but in which each waveguiding region has its own individual grating.

The physically or optically separate waveguiding regions can be produced using known methods. There are two possible basic methods. For example, a) the layers can be built up physically separately from the beginning in a vapour deposition method using masks or b) a continuous layer is produced and then structured using suitable methods.

An example of method a) is the vapour deposition of the inorganic waveguiding material, with a suitably structured mask covering part of the sensor platform. Such masks are known from the production of integrated circuits. The masks should be in direct contact with the sensor platform. Positive and negative masks can be used.

It is also possible to apply a suspension of the inorganic waveguiding material to the sensor platform through a suitably structured mask and to produce the waveguiding layer by the sol-gel technique.

In that manner separate waveguiding regions are formed, the division being effected in the simplest case by means of an air gap. That gap can, however, be filled subsequently with a different material of lower refractive index than that of the waveguiding layer. If the division into several waveguiding regions is carried out in that manner, the difference in effective refractive index between the waveguiding region and the adjacent material is preferably more than 0.2, especially more than 0.6, units.

An example of method b) is the vapour deposition of an inorganic waveguiding material to form a continuous layer which is then divided into individual waveguiding regions by mechanical scratching, laser material machining, lithographic processes or plasma processes.

The vapour deposition is generally carried out under vacuum conditions. Plasma deposition is likewise possible.

Special mention should be made of machining using pulsed excimer and solid state lasers or continuous gas lasers. In the case of pulsed high-energy lasers the structuring can be effected over a large area through a mask. In the case of continuously operating lasers, the focused beam is generally passed over the waveguiding layer to be structured, or the waveguiding layer is moved relative to the beam.

Suitable lithographic processes are etching techniques, such as those used in the production of printed circuit boards or microelectronics components. Those processes allow an extraordinarily wide variety of geometric patterns and a fineness of structure in the micrometer or submicrometer range.

It is important in the case of any ablative machining process for the waveguiding layer to be partially or completely removed, but without the sensor platform being divided completely. Any intermediate layers that may be present can likewise be completely or partially removed.

In a modified form of method b), a continuous layer of an inorganic waveguiding material is applied first and then in a second step, using an absorbing material that interrupts the waveguiding, a structure is applied to that layer in such a manner that waveguiding regions are divided by absorbing, and hence non-waveguiding, regions.

The absorbing materials may be inorganic materials, such as metals having a high optical absorption coefficient, e.g. gold, silver, chromium or nickel, or organic compounds, for example dyed and pigmented polymers. Those materials can be applied to the waveguiding layer in the form of continuous layers or, as is the case with the metals, in the form of aqueous colloidal solutions. A selection of different methods is available.

Deposition processes for structuring that are carried out under vacuum conditions have already been mentioned above.

Colloidal materials in water or organic solvents, such as gold in water, can likewise be used for structuring waveguiding regions.

The deposition of colloidal gold on surfaces by means-of spontaneous 'assembly' has been described, for example, by R. Griffith et al, Science 1995, 267, 1629–1632. For example, physically or fluidically separate laminar part streams of a colloidal gold solution can be allowed to flow over the waveguiding layer, the gold particles being deposited, for example, in the form of strips. The surface is dried, and separate, waveguiding regions according to the invention are obtained. The deposited gold colloids must have a minimum size of from 10 to 15 nm in order for the desired absorption to occur. They are preferably from 15 to 35 nm in diameter.

The deposition of colloidal gold can also be effected by stamping onto the surface. The stamping of dissolved organic materials is described by Whitesides as 'microcontact printing' and has been used for structuring gold surfaces using liquid alkanethiols (J. L. Wilbur et al., Adv. Mater. 1994, 6, 600–604; Y. Xia and G. M. Whitesides, J. Am. Chem. Soc. 1995, 117, 3274–3275). For example, colloidal gold solution can be aspirated into an elastomeric stamp having the desired structuring pattern and the structuring pattern can be transferred to the waveguiding surface by applying the stamp.

Methods that use organic solvents or water are very flexible and quick to use. They allow waveguide structuring to be effected immediately before a luminescence assay is carried out.

In some cases the surface of the waveguiding layer has to be modified in such a manner before the colloidal deposition of, for example, gold that good adhesion results between the colloid particles and the modified surface. The adhesion can be achieved by means of hydrophobic interaction, van der Waals forces, dipole-dipole interaction, simple electrostatic interaction or by means of covalent bonding. The interaction can be produced by functionalisation of the colloids and/or of the surface of the waveguiding layer.

A suitable method of modifying the surface and of achieving adhesion is, for example, silanisation as described in Advances in Colloid and Interface Science 6, L. Boksányi, O. Uardon and E. Kováts, (1976) 95–137. Such silanisation is used also to improve the adhesion of the recognition elements in affinity sensing. In particular, mercapto-terminated silane, such as (mercaptomethyl) dimethylethoxysilane, is suitable for bringing about the adhesion of gold by means of the formation of a covalent sulfur-gold bond.

Another modification of method b) consists in applying to the continuous layer of inorganic waveguiding material, in a second step, the same inorganic material in the form of a structure, with the result that by increasing the layer thickness an increase in the effective refractive index is achieved and thus the propagation of the lightwave mode is concentrated in the resulting measuring regions. Such 'slab waveguides' and methods of producing them are described by H. P. Zappe in 'Introduction to Semiconductor Integrated Optics', Artech House Inc., 1995.

The strip width of the waveguiding layers is preferably from 5 micrometers to 5 millimeters, especially from 50 micrometers to 1 millimeter.

If the width of the waveguiding regions is reduced too far, the available sensor area will also be reduced. Advantageously, the strip width and the area of sensor required are matched to one another.

The size and width of the individual waveguiding regions can be varied within a wide range and depend substantially on the intended use and on the structure of the system as a whole.

When they are in the form of strips, the individual waveguiding regions are preferably from 0.5 to 50 mm, especially from 1 to 20 mm, and very especially from 2 to 10 mm, in length.

The number of strips on the sensor platform is preferably from 2 to 1000, especially from 2 to 100.

The individual waveguiding regions can be arranged, for example, as strips on the substrate in two or more groups of at least two strips each, thus forming a multiple detection region.

The great practical advantage of such assembled multiple detection regions is that the sensor platform does not need to be cleaned or replaced between successive multianalyte measurements, but merely has to be displaced relative to the excitation, fluidic and detection units.

A further advantage is that such multiple detection regions are more economical to produce. A very substantial advantage is the fact that the very time-consuming and cost-intensive separation into divided sensor platforms is not required.

Each multiple detection region preferably consists of from 2 to 50, especially from 2 to 20, separate waveguiding regions.

There are preferably from 2 to 100, especially from 5 to 50, multiple detection regions on the sensor platform.

Figure 3B:
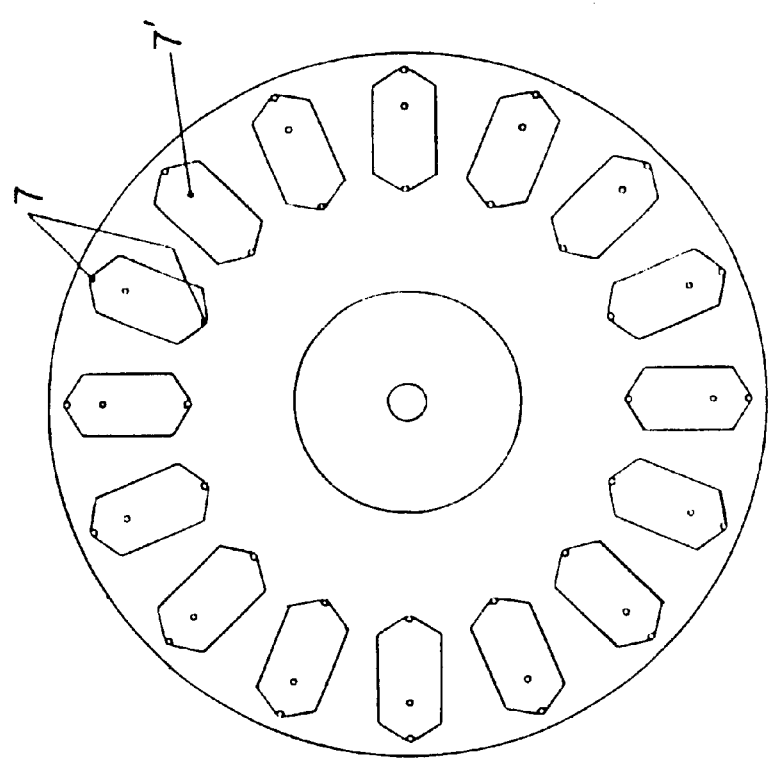
FIGS. 3a–3b and 4a–4b show a possible arrangement of a sensor platform on a disc having a plurality of multiple detection regions.
Figure 3A:
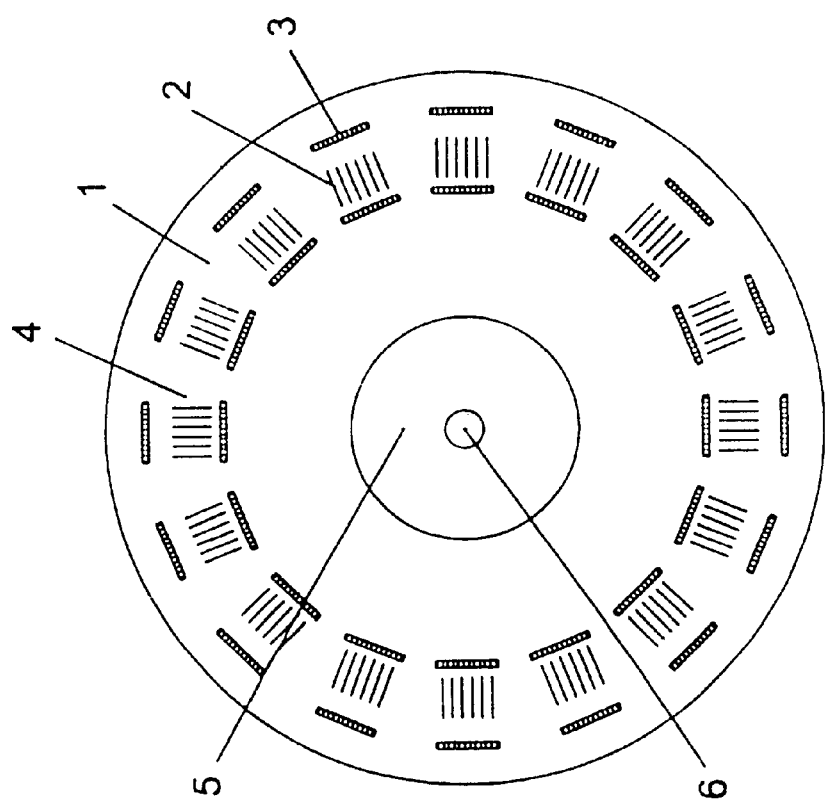

FIGS. 3a and 3b show a possible arrangement of a sensor platform having a plurality of multiple detection regions, in which the substrate is in the form of a disc and which can be produced by means of press moulding in a manner similar to that currently used for compact discs. The overall arrangement may consist of a disc-like sensor platform having a plurality of multiple detection regions and a fluidics disc that comprises the fluid supply lines and the actual cell spaces. The two parts are joined, for example glued, together and form a unit.

However, the cell spaces in the form of wells can alternatively be preformed in the disc-like sensor platform. Such an embodiment is then covered with a planar lid.

The reference numerals 1 to 3 are as defined above, 4 denotes a complete multiple detection region, 5 is the substrate and 6 is a central cut-out portion that can accommodate an axle to enable the individual multiple detection regions 4 to be passed, by rotation, under excitation and detection optics. 7 and 7' denote inlet and outlet openings for the solutions required in the course of the assay, which solutions are generally brought into contact, via a through-flow cell having at least two openings, with the recognition elements immobilised on the waveguiding regions.

The multiple detection regions may alternatively be arranged in concentric circles. The distances between the individual multiple detection regions may, for example, be such that rotation through an angle of from 5 to 20 degrees brings a new multiple detection region under the excitation and detection optics.

Figure 4B:
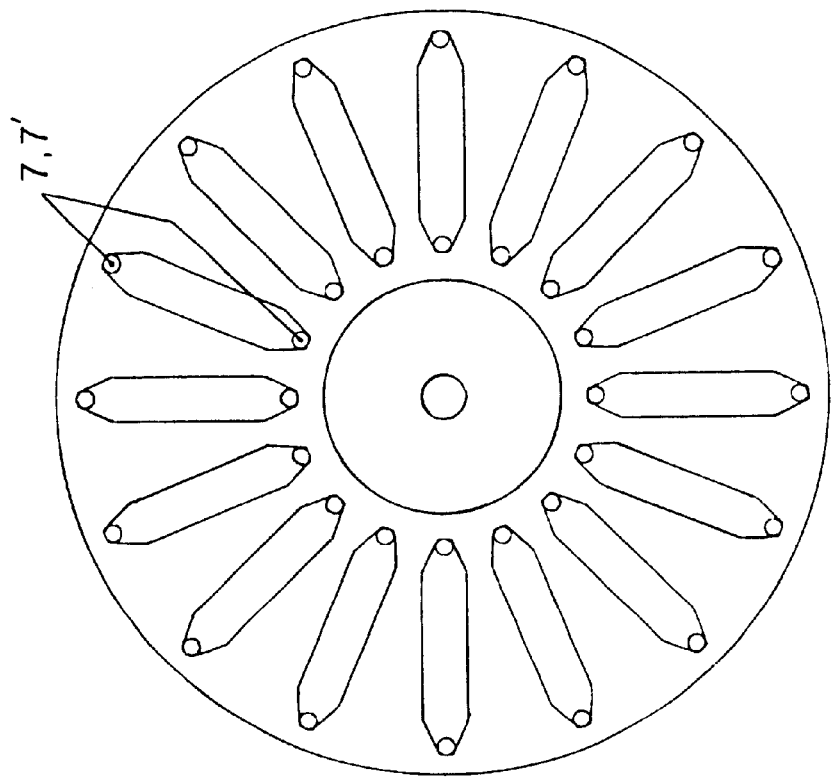
Figure 4A:
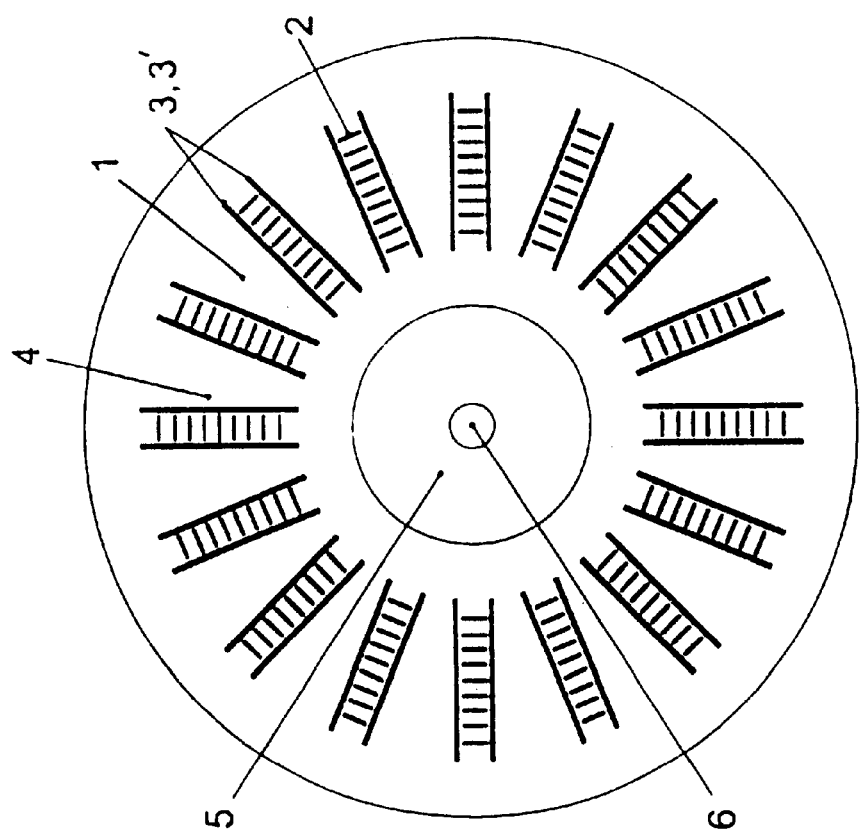

FIGS. 4a and b show an analogous construction of the sensor platform on a disc, with the difference that, in comparison with FIG. 3, the individual multiple detection regions 4 are arranged radially rather than tangentially, which leads to improved utilisation of the surface area.

Figure 5B:
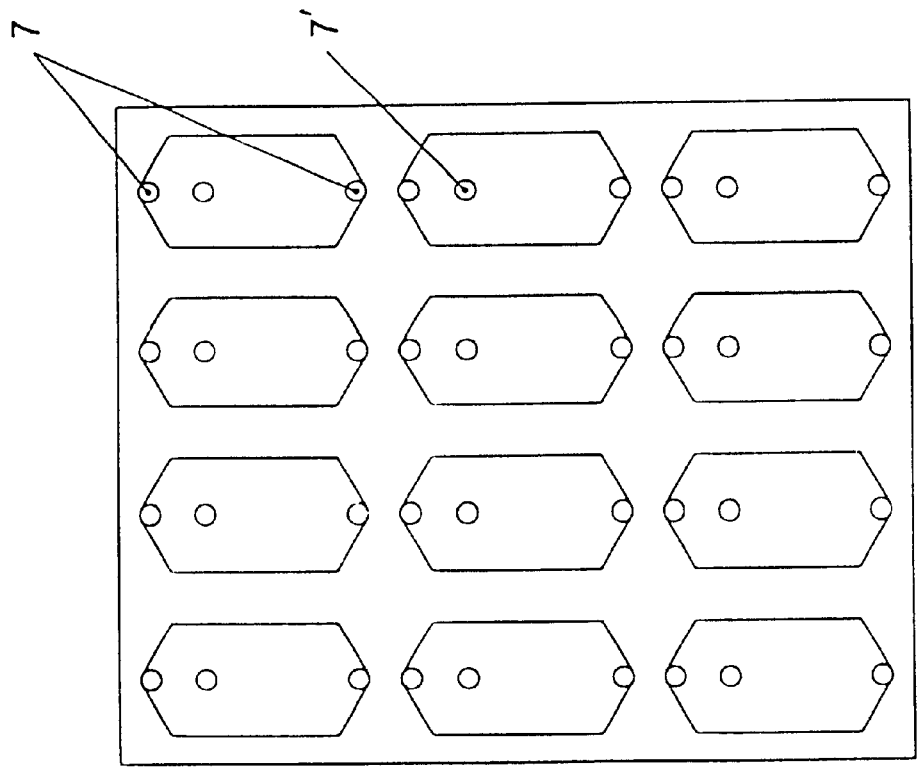
FIGS. 5a–5b show a possible arrangement of a sensor platform on a rectangular chessboard pattern having a plurlity of multiple detection regions.
Figure 5A:
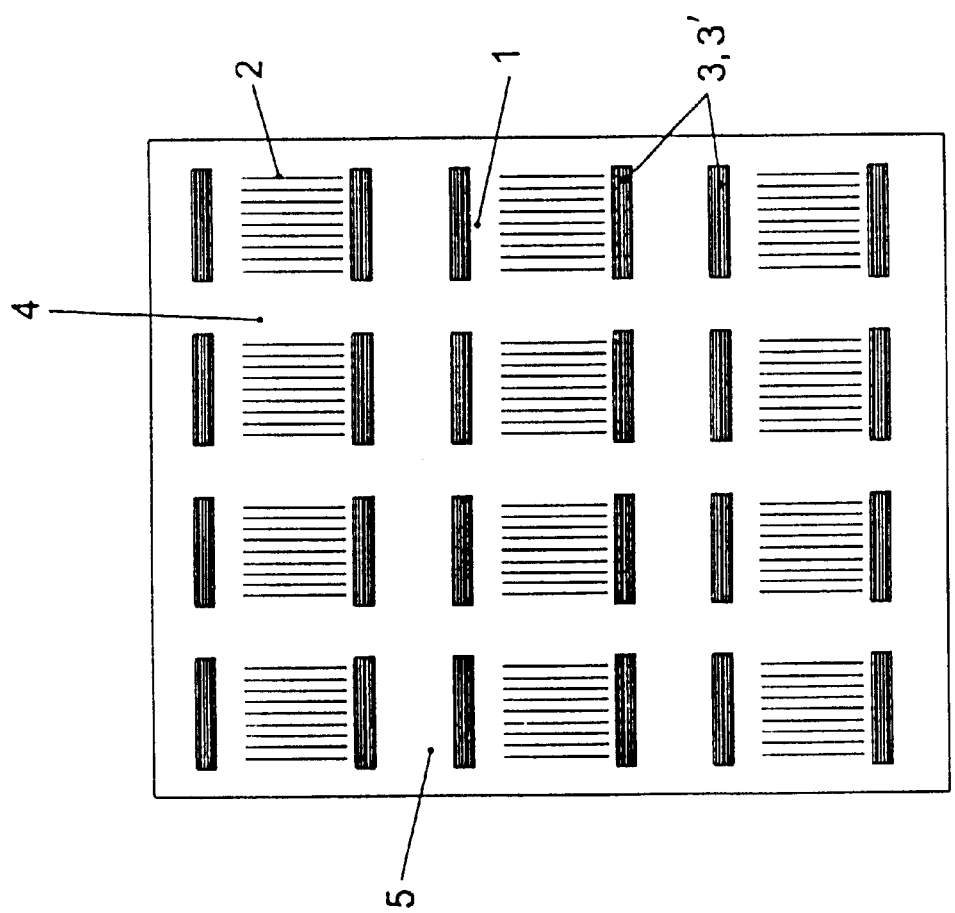

A further arrangement is shown in FIGS. 5a and 5b. The individual multiple detection regions 4 are arranged in the form of a rectangular chessboard pattern. The multiple detection regions can, however, also be arranged in the manner of individual images in a film strip.

The film strip may be in the form of a planar element or may be rolled up.

The individual multiple detection regions can be transported under excitation and detection optics in a manner analogous to a film.

The preferences indicated for the separate waveguiding regions apply also in the case of the multiple detection regions.

A sensor platform within the context of the present invention is a self-supporting element that can be constructed in the form of a strip, a plate, a round disc or any other desired geometric form. It is essentially planar. The geometric form selected is in itself non-critical and can be chosen to suit the structure of the apparatus as a whole in which the sensor platform is installed. The sensor platform can, however, also be used as an independent element, physically separate from an excitation light source and from the optoelectronic detection system. Preference is given to arrangements that allow substantial miniaturisation.

Suitable substrates are, for example, glass of all types or quartz. Preferably, glass that has the lowest possible optical refractive index and the lowest possible degree of intrinsic luminescence and that allows the simplest possible optical machining, such as etching, grinding and polishing, is used.

The substrate is preferably transparent, at least at the excitation and emission wavelengths. The microscopic roughness of the substrate should be as low as possible.

There may also be used as substrates transparent thermoplastic plastics, such as those described, for example, in EP-A-0 533 074.

The substrates may additionally be covered with a thin layer that has a refractive index lower than or equal to that of the substrate and is not thicker than 0.01 mm. That layer can be used to prevent troublesome fluorescence excitation in the substrate and also to reduce the surface roughness of the substrate and may consist of thermoplastic, thermally crosslinkable or structurally crosslinked plastics or alternatively of inorganic materials such as $SiO_2$.

In the presence of an intermediate layer, with a refractive index lower than the one of the waveguiding layer and with a layer thickness considerably larger than the penetration depth of the evanescent field (i.e., >>100 nm), transparency of only this intermediate layer, at the excitation and emission wavelength, is sufficient, if the excitation light is launched from the top side of the sensor platform. In this case the substrate can also be absorbent.

Especially preferred substrate materials consisting of transparent thermoplastic plastics are polycarbonate, polyimide or polymethylmethacrylate.

The refractive index is preferably the same for all waveguiding layers, that is to say all the waveguiding layers are preferably made from the same material.

The refractive index of the waveguiding layers must be greater than that of the substrate and of any intermediate layers that are used. The planar, transparent, waveguiding layer preferably consists of a material having a refractive index greater than 2.

There are suitable, for example, inorganic materials, especially inorganic metal oxides, such as $TiO_2$, $ZnO$, $Nb_2O_5$, $Ta_2O_5$, $HfO_2$ or $ZrO_2$.

$Ta_2O_5$ and $TiO_2$ are preferred.

The thickness of the waveguiding layers is preferably from 40 to 1000 nm, especially from 40 to 300 nm and very especially from 40 to 160 nm.

In a preferred embodiment, the waveguiding layers are of the same thickness.

The modulation depth of the gratings is preferably from 3 to 60 nm, especially from 3 to 30 nm.

The ratio of the modulation depth to the thickness of the layers is preferably equal to or less than 0.5 and especially equal to or less than 0.2.

The gratings for coupling in the excitation light or for coupling out the backcoupled luminescence light are in the form of optical diffraction gratings, preferably in the form of relief gratings. The relief structure may have various forms. There are suitable, for example, sinusoidal, rectangular or sawtooth structures. Processes for the production of such gratings are known. There are used predominantly for their production photolithographic or holographic processes and etching techniques, such as those described, for example, in Chemical, Biochemical and Environmental Fiber Sensors V. Proc. SPIE, Vol 2068, 313–325, 1994. Moulding or stamping processes can also be used for organic substrates.

The grating structure can be produced on the substrate and then transferred to the wave-guiding layer, where the grating structure then reproduces itself, or the grating is produced in the waveguiding layer itself.

The grating period may be from 200 to 1000 nm, grating advantageously having only one periodicity, that is to say being monodiffractive. The grating period selected is preferably one that allows the excitation light to be coupled in in the first diffraction order.

The modulation depths of the gratings are preferably of the same magnitude.

The gratings preferably have a bar-to-space ratio of from 0.5 to 2. By "bar-to-space ratio" there is to be understood, for example in the case of a rectangular grating, the ratio of the width of the bars to the width of the spaces.

The gratings can be used both for coupling excitation light into the individual waveguiding layers and for coupling out luminescence light backcoupled into the waveguiding layers.

For the analysis of samples of different luminescences, it may be advantageous for all or some of the coupling-in and coupling-out gratings to have different grating constants.

In a preferred embodiment, the grating constants are the same for all gratings.

If some of the gratings are used to couple in and some to couple out the light, the grating constant of the coupling-in grating or gratings is preferably different from the grating constant of the coupling-out grating or gratings.

The grating spacing is preferably $B \leq 3 \cdot X_{1/e}$, $X_{1/e}$ being the length at which the intensity $I_0$ of the guided radiation has fallen to $I_0/e$.

In a preferred group of embodiments of the sensor platform:

the transparent, planar, inorganic dielectric waveguiding regions on the sensor platform are divided from one another at least along the measuring section by a jump in refractive index of at least 0.6 and each region has one or two separate grating couplers or all regions together have one or two common grating couplers, the transparent, planar, inorganic dielectric waveguiding regions having a thickness of from 40 to 160 nm, the modulation depth of the gratings being from 3 to 60 nm and the ratio of modulation depth to thickness being equal to or less than 0.5.

The simplest method of achieving a jump in refractive index of 0.6 or more is for the wave-guiding layer to be divided completely and to contain an air gap or, during measurement, optionally water.

The waveguiding layers preferably guide only from 1 to 3 modes and are especially mono-modal waveguides.

A further subject of the invention is a modified sensor platform wherein there are immobilised on the surface of the waveguiding regions one or more specific binding partners as chemical or biochemical recognition elements for one or more identical or different analytes.

Various specific binding partners can be applied to the surface of a waveguiding region, the physical separation thereof within each waveguiding region being unimportant. They can, for example, be present thereon in the form of a random mixture. That is advantageous when analytes having different emission wavelengths are to be determined simultaneously by way of a coupling-out grating.

The specific binding partners on the surface of each waveguiding region are preferably physically separate from one another.

The specific binding partners can be immobilised at various sites on the waveguiding regions, for example by photochemical crosslinking, as described in WO 94/27137. Another method comprises the dropwise application of the specific binding partners that are to be immobilised, using a multiple-pipette head. That can also be effected using a modified inkjet printing head with piezoelectric actuators. That has the advantage that the method can be carried out rapidly and that very small amounts can be used. That is a precondition for the production of thin strips or other finely structured geometric patterns.

Another preferred method for the physically separate immobilisation of the specific binding partners on the waveguiding regions that is very simple to carry out is based on the use of a flow cell, it being possible for the separation to be effected in the flow cell, either mechanically in the form of dividing bars or fluidically in the case of laminar flow. In that method the geometric arrangement of the part streams supplying the binding partners corresponds substantially to the arrangement of the waveguiding regions on the sensor platform. That method of immobilisation using a flow cell is advantageous especially when the specific binding partners are to be embedded in an environment that is stable only in the fluid medium, as is the case, for example, with lipid-membrane-bound receptors.

In particular, it is possible in that manner to deposit specific binding partners that are covalently bonded to gold colloids, in the same manner as described above for the production of non-waveguiding regions. In order to obtain waveguiding in the immobilisation regions, it is necessary to use gold colloids of very small diameters of less than 10 nm and especially of less than 5 nm.

A further method that is likewise simple to carry out is based on stamping the surface with the specific binding partners, or with specific binding partners bonded to metals, in a manner analogous to that described above for the production of non-waveguiding regions.

A preferred metal is gold.

Preferred physically separate patterns are strips, rectangles, circles, ellipses or chessboard patterns.

Preference is given especially to a modified sensor platform wherein only one specific binding partner is arranged on the surface of each waveguiding region.

Another preferred embodiment of the modified sensor platform is obtained if an adhesion-promoting layer is located between the waveguiding regions and the immobilised specific binding partners.

The thickness of the adhesion-promoting layer is preferably equal to or less than 50 nm, especially less than 20 nm.

It is possible, furthermore, for adhesion-promoting layers to be applied selectively only in the waveguiding regions or to be passivated in the non-waveguiding regions, for example by means of photochemical activation or using wet-chemical methods, such as a multiple-pipette head, inkjet printers, flow cells with mechanical or fluidic separation of the streams, deposition of colloids or stamping of the surface. The methods have already been described above for the direct immobilisation of the specific recognition elements on an optionally chemically modified or functionalised surface.

The selective immobilisation of the specific recognition elements exclusively on the wave-guiding regions, either directly or by way of adhesion-promoting layers, can, when using a sample cell that covers both the waveguiding and the non-waveguiding regions, lead to an increase in the sensitivity of the detection method, since the non-specific binding of the analytes in the regions not used for signal generation is reduced.

The preferences described hereinbefore for the sensor platform apply likewise to the modified sensor platform.

The modified sensor platform is preferably fully or partially regenerable and can be used several times. Under suitable conditions, for example at low pH, at elevated temperature, using organic solvents, or using so-called chaotropic reagents (salts), the affinity complexes can be selectively dissociated without substantially impairing the binding ability of the immobilised recognition elements. The precise conditions are greatly dependent upon the individual affinity system.

A specific form of luminescence detection in an assay consists in the immobilisation of the luminescent substances that are used for detection of the analyte directly on the surface of the waveguiding regions. Those substances may be, for example, a plurality of luminophores bound to a protein which can thus be excited to luminescence on the surface of the waveguiding regions. If partners having affinity for the proteins are passed over that immobilised layer, the luminescence can be altered thereby and the quantity of partners having affinity can thus be determined. In particular, it is also possible for both partners of an affinity complex to be labelled with luminophores in order, for example, to carry out determinations of concentration on the basis of the energy transfer between the two, for example in the form of luminescence extinction.

Another, preferred form of immobilisation for chemical or biochemical affinity assays consists in the immobilisation on the surface of the sensor platform of one or more specific binding partners as chemical or biochemical recognition elements for the analytes themselves or for one of the binding partners. The assays may consist of one or more stages in the course of which, in successive steps, one or more solutions containing specific binding partners for the recognition elements immobilised on the surface of the sensor platform can be passed over the surface of the sensor platform, the analytes being bound in one of the part steps. The analytes are detected by the binding of luminescently labelled participants in the affinity assay. The luminescence-labelled substances may be any one or more of the binding partners of the affinity assay, or an analogue of the analytes provided with a luminophore. The only precondition is that the presence of the analytes should lead selectively to a luminescence signal or selectively to a change in the luminescence signals.

In order to increase the chemically active sensor surface, it is also possible to immobilize the chemical or biochemical recognition elements on micro particles, so-called "beads", which can be fixed on the sensor platform by adequate methods. Prerequesites for the use of beads, which can consist of different materials, such as plastics, are that, first, the interaction with the analytes procedes, to a significant extent, within the penetration depth of the evanescent field, and that, second, the waveguiding properties are not significantly interfered.

In principle, the recognition elements can be immobilised, for example, by hydrophobic adsorption or covalent bonding directly on the waveguiding regions or after chemical modification of the surface, for example by silanisation or the application of a polymer layer. In addition, in order to facilitate the immobilisation of the recognition elements directly on the waveguide, a thin intermediate layer, for example consisting of $SiO_2$, can be applied as adhesion-promoting layer. The silanisation of glass and metal surfaces has been described comprehensively in the literature, for example in Advances in Colloid and Interface Science 6, L. Boksányi, O. Liardon and E. Kováts, (1976) 95–137. Specific possible methods of carrying out the immobilisation have already been described hereinbefore.

Suitable recognition elements are, for example, antibodies for antigens, binding proteins, such as protein A and G, for immunoglobulins, biological and chemical receptors for ligands, chelators for histidine-tag components, for example histidine-labelled proteins, oligonucleotides and single strands of RNA or DNA for their complementary strands, avidin for biotin, enzymes for enzyme substrates, enzyme cofactors or inhibitors, or lectins for carbohydrates. Which of the relevant affinity partners is immobilised on the surface of the sensor platform depends on the architecture of the assay. The recognition elements may be natural or may be produced or synthesised by means of genetic engineering or biotechnology.

The expressions "recognition element" and "specific binding partner" are used synonymously.

The assays themselves may be either one-step complexing processes, for example competitive assays, or multi-step processes, for example sandwich assays.

In the simplest example of a competitive assay, the sample, which comprises the analyte in unknown concentration and a known amount of a compound that is identical apart from being luminescence-labelled, is brought into contact with the surface of the sensor platform, where the luminescence-labelled and unlabelled molecules compete for the binding sites on their immobilised recognition elements. In this assay configuration, a maximum luminescence signal is obtained when the sample contains no analyte. As the concentration of the substance to be detected increases, the observable luminescence signals decrease.

In a competitive immunoassay, the recognition element immobilised on the surface of the sensor platform does not have to be the antibody but may alternatively be the antigen. It is generally a matter of choice in chemical or biochemical affinity assays which of the partners is immobilised. That is one of the principal advantages of assays based on luminescence over methods such as surface plasmon resonance or interferometry which rely on a change in the adsorbed mass in the evanescent field of the waveguiding region.

Furthermore, the competition in the case of competitive assays need not be limited to binding sites on the surface of the sensor platform. For example, a known amount of an antigen can be immobilised on the surface of the sensor platform and then brought into contact with the sample which comprises as analyte an unknown amount, which is to be detected, of the same antigen and also luminescence-labelled antibodies. In that case, the competition to bind the antibodies takes place between antigens immobilised on the surface and antigens in solution.

The simplest example of a multi-step assay is a sandwich immunoassay in which a primary antibody is immobilised on the surface of the sensor platform. The binding of the antigen to be detected and of the luminescence-labelled secondary antibody used for the detection to a second epitope of the antigen can be effected either by contact with, in succession, the solution comprising the antigen and a second solution comprising the luminescence-labelled antibody or after previously bringing the two solutions together so that finally the part-complex consisting of antigen and luminescence-labelled antibody is bound.

Affinity assays may also comprise further additional binding steps. For example, in the case of sandwich immunoassays, in a first step protein A can be immobilised on the surface of the sensor platform. The protein specifically binds immunoglobulins to its so-called $F_c$ portion and these then serve as primary antibodies in a subsequent sandwich assay which can be carried out as described.

There are many other forms of affinity assay, for example using the known avidin-biotin affinity system.

Examples of forms of affinity assay are to found in J. H. Rittenburg, Fundamentals of Immunoassay; in Development and Application of Immunoassay for Food Analysis, J. H. Rittenburg (Ed.), Elsevier, Essex 1990, or in P. Tijssen, Practice and Theory of Enzyme Immunoassays, R. H. Burdon, P. H. van Knippenberg (Eds), Elsevier, Amsterdam 1985.

A further subject of the invention is a method for the parallel determination of one or more luminescences using a sensor platform or modified sensor platform according to the invention, which method comprises bringing one or more liquid samples into contact with one or more waveguiding regions on the sensor platform, coupling excitation light into the waveguiding regions, causing it to pass through the waveguiding regions, thus exciting in parallel in the evanescent field the luminescent substances in the samples or the luminescent substances immobilised on the waveguiding regions and, using optoelectronic components, measuring the luminescences produced thereby.

The preferences described hereinbefore for the sensor platform and the modified sensor platform apply also to the method.

Only substantially parallel light is suitable for luminescence excitation. "Substantially parallel" is to be understood within the context of this invention to mean a divergence of less than 5°. That means that the light may be slightly divergent or slightly convergent. The use of coherent light for the luminescence excitation is preferred, especially laser light having a wavelength of from 300 to 1100 nm, more especially from 450 to 850 nm and most especially from 480 to 700 nm.

Examples of lasers that may be used are dye lasers, gas lasers, solid state lasers and semiconductor lasers. If necessary, the emission wavelength can also be doubled by means of non-linear crystal optics. Using optical elements the beam can also be focused further, polarised or attenuated by means of neutral grey filters. Especially suitable lasers are argon/ion lasers and helium/neon lasers which emit at wavelengths of from 457 nm to 514 nm and from 543 nm to 633 nm, respectively. Very especially suitable are diode lasers or frequency-doubled diode lasers of semiconductor material that emit at a fundamental wavelength of from 630 nm to 1100 nm since, owing to their small dimensions and low power consumption, they allow substantial miniaturisation of the sensor system as a whole.

By "sample" there is to be understood within the context of the present invention the entire solution to be analysed, which may comprise a substance to be detected—the analyte. The detection can be effected in a one-step or multiple-step assay during the course of which the surface of the sensor platform is brought into contact with one or more solutions. At least one of the solutions used comprises a luminescent substance which can be detected according to the invention.

If a luminescent substance has already been adsorbed onto the waveguiding region, the sample may also be free of luminescent constituents. The sample may contain further constituents, such as pH buffers, salts, acids, bases, surfactants, viscosity-influencing additives or dyes. In particular, a physiological saline solution can be used as solvent. If the luminescent portion is itself liquid, the addition of a solvent can be omitted. In that case the content of luminescent substance in the sample may be up to 100%.

The sample may also be a biological medium, such as egg yolk, a body fluid or the components thereof, especially blood, serum, plasma or urine. It may also be surface water, solutions of extracts from natural or synthetic media, such as soils or parts of plants, liquors from biological processes or synthetic liquors.

The sample may be used either undiluted or with added solvent.

Suitable solvents are water, aqueous buffer solutions and protein solutions and organic solvents. Suitable organic solvents are alcohols, ketones, esters and aliphatic hydrocarbons. Preference is given to the use of water, aqueous buffers or a mixture of water with a miscible organic solvent.

However, the sample may also comprise constituents that are not soluble in the solvent, such as pigment particles, dispersants and natural and synthetic oligomers or polymers. The sample is then in the form of an optically opaque dispersion or emulsion.

There may be used as luminescent compounds functionalised luminescent dyes having a luminescence of a wavelength in the range of from 330 nm to 1000 nm, such as rhodamines, fluorescein derivatives, coumarin derivatives, distyryl biphenyls, stilbene derivatives, phthalocyanines, naphthalocyanines, polypyridyl/ruthenium complexes, such as tris(2,2'-bipyaidyl) ruthenium chloride, tris(1,10-phenanthroline)ruthenium chloride, tris(4,7- diphenyp-1,10-phenanthroline) ruthenium chloride and polypyridyl/phenazine/ruthenium complexes, platinum/porphyrin complexes, such as octaethyl-platinum-porphyrin, long-lived europium and terbium complexes or cyanine dyes. Especially suitable for analyses in blood or serum are dyes having absorption and emission wavelengths in the range of from 600 to 900 nm.

Very especially suitable are dyes, such as fluorescein derivatives, containing functional groups by means of which they can be covalently bonded, such as fluorescein isothiocyanate.

Also very suitable are the functional fluorescent dyes that are commercially available from Biological Detection Systems Inc., for example the mono- and bifunctional Cy5.5® dyes, which are also described, for example, in Clinical Chemistry 40 (9): 1819–1822, 1994.

The preferred luminescence is fluorescence.

The use of different fluorescent dyes that can all be excited by light of the same wavelength, but have different emission wavelengths, may be advantageous, especially when using coupling-out gratings.

The luminescent dyes used may also be chemically bonded to polymers or to one of the binding partners in biochemical affinity systems, for example antibodies or antibody fragments, antigens, proteins, peptides, receptors or their ligands, hormones or hormone receptors, oligonucleotides, DNA strands and RNA strands, DNA or RNA analogues, binding proteins, such as protein A and G, avidin or biotin, enzymes, enzyme cofactors or inhibitors, lectins or carbohydrates. The use of the last-mentioned covalent luminescence labelling is preferred for reversible or irreversible (bio)chemical affinity assays. It is also possible to use luminescence-labelled steroids, lipids and chelators. In the case especially of hybridisation assays with DNA strands or oligonucleotides, intercalating luminescent dyes are also especially suitable, especially when—like various ruthenium complexes—they exhibit enhanced luminescence when intercalated. When those luminescence-labelled compounds are brought into contact with their affinity partners immobilised on the surface of the sensor platform, their binding can be readily quantitatively determined using the measured luminescence intensity. Equally, it is possible to effect a quantitative determination of the analytes by measuring the change in luminescence when the sample interacts with the luminophores, for example in the form of luminescence extinction by oxygen or luminescence enhancement resulting from conformation changes in proteins.

In the method according to the invention, the samples can either be brought into contact with the waveguiding regions when stationary or be passed over them continuously, it being possible for the circulation to be open or closed.

A further important form of application of the method is based firstly on limiting the generation of signals—in the case of backcoupling that applies also to signal detection—to the evanescent field of the waveguide and secondly on the reversibility of the affinity complex formation as an equilibrium process. Using suitable flow rates in a throughflow system, the binding or desorption, i.e. dissociation, of bound, luminescence-labelled affinity partners in the evanescent field can be followed in real time. The method is therefore suitable for kinetic studies for determining different association or dissociation constants or for displacement assays.

The evanescently excited luminescence can be detected by known methods. Suitable are photodiodes, photocells, photomultipliers, CCD cameras and detector arrays, such as CCD rows and CCD arrays. The luminescence can be projected onto the latter by means of optical elements, such as mirrors, prisms, lenses, Fresnel lenses and graded-index lenses, it being possible for the elements to be arranged individually or in the form of arrays. In order to select the emission wavelength, known elements, such as filters, prisms, monochromators, dichroic mirrors and diffraction gratings can be used.

Especially when a relatively large number of physically separate specific binding partners is; present, the use of detector arrays arranged in the immediate vicinity of the sensor platform is advantageous. There are advantageously arranged between the sensor platform and the) detector array optical elements for separating excitation and luminescence light, such as holographic or interference filters.

A form of the method consists in detecting the isotropically radiated, evanescently excited luminescence.

In another form of the method, the evanescently excited luminescence backcoupled into the waveguiding region is detected at an edge of the sensor platform or via a coupling-out grating. The intensity of the backcoupled luminescence is surprisingly high, with the result that very good sensitivity can likewise be achieved using that procedure.

In another form of the method, both the evanescently excited, isotropically radiated luminescence and the luminescence backcoupled into the waveguide are detected independently of one another but simultaneously. Owing to the different selectivity of those two luminescence detection methods, which selectivity is a function of the distance between the luminophores and the waveguiding region, this form of the method can be used to obtain additional information relating to the physical distribution of the luminophores. That also makes it possible to distinguish between photochemical bleaching of the luminophores and dissociation of the affinity complexes carrying the luminophores.

Another advantage of the method is that, in addition to the detection of luminescence, the absorption of the excitation light radiated in can be determined simultaneously. Compared with multimodal waveguides of fibre optic or planar construction, in this case a substantially better signal/noise ratio is achieved. Luminescence extinction effects can be detected with great sensitivity by means of the simultaneous measurement of luminescence and absorption.

The method can be carried out by radiating in the excitation light in continuous wave (cw) operation, i.e. the excitation is effected with light of an intensity that is constant over time.

However, the method can also be carried out by radiating in the excitation light in the form of a timed pulse having a pulse length of, for example, from one picosecond to 100 seconds and detecting the luminescence in a time—resolved manner—in the case of short pulse lengths—or at intervals of from seconds to minutes. That method is especially advantageous when, for example, the rate of formation of a bond is to be followed analytically or the reduction in a luminescence signal resulting from photochemical bleaching is to be prevented using short exposure times. Furthermore, the use of suitably short pulse lengths and suitable time resolution of the detection make possible the discrimination of scattered light, Raman emission and short-lived luminescence of any undesired luminescent constituents of the sample or of the sensor material that may be present from the luminescence of the labelling molecule (which in this case is as long-lived as possible), since the emission of the analyte is detected only once the short-lived radiation has decayed. In addition, time-resolved luminescence detection after pulsed excitation, and, likewise, modulated excitation and detection, allows investigation of the influence of the binding of the analyte on molecular luminescence decay behavior. The molecular luminescence decay time can be used, alongside specific analyte recognition by the immobilised recognition elements and physical limitation of the generation of signals to the evanescent field of the waveguide, as a further selectivity criterion.

The method can also be carried out by radiating in the excitation light in an intensity modulated manner, at one or more frequencies, and detecting the resulting phase shift and modulation of the luminescence of the sample.

Parallel coupling of excitation light into a plurality of waveguiding regions can be carried out in several ways:
a) a plurality of laser light sources are used;
b) the beam from a laser light source is broadened using known suitable optical components so that it covers a plurality of waveguiding regions and coupling-in gratings;
c) the beam from a laser light source is split using diffractive or holographically optical elements into a plurality-of individual beams which are then coupled into the waveguiding regions via the gratings, or
d) an array of solid state lasers is used.

An advantageous procedure also is obtained by using a controllable deflecting mirror which can be used for coupling into or out of the waveguiding regions with a time delay. Alternatively, the sensor platform can be suitably displaced.

Another preferred method consists in exciting the luminescences with various laser light sources of identical or different wavelengths.

Preference is given especially to the use of a single row of diode lasers (laser array) for the excitation of the luminescences. Those components have the special advantage that they are very compact and economical to produce, and the individual laser diodes can be individually controlled.

The preferences described for the sensor platform apply also in the case of the fluorescence detection method.

Figure 6:
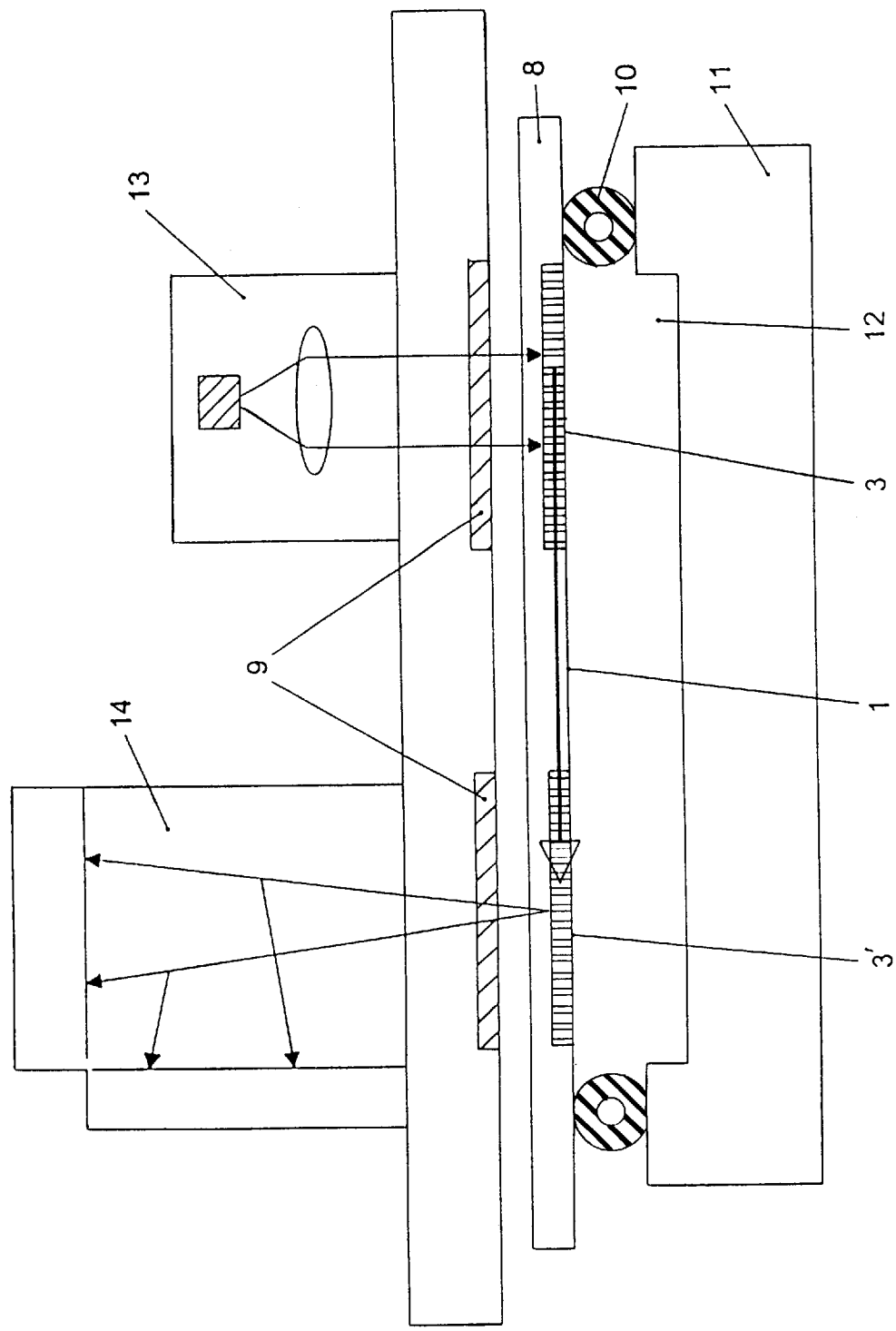
FIG. 6 shows a diagrammatic representation of a possible overall construction of the present invention.

FIG. 6 is a diagrammatic representation of a possible overall construction. Reference numerals 1 and 3 are as defined hereinbefore and other reference numerals are as follows:
8 sensor platform
9 filters
10 seal
11 throughflow cell
12 sample space
13 excitation optics
14 detection optics/electronics The excitation light, for example from a diode laser 13, is coupled via a first grating 3 into a waveguiding region 1 of the sensor platform 8. On the underside of the sensor platform 8 and pressed tightly against the sensor platform is a throughflow cell 11. The solutions required for the assay are flushed through the space 12 in the throughflow cell 11, which may have one or more inlet openings and one or more outlet openings. The fluorescence of a binding partner is detected at the detector 14 onto which the fluorescence light back-coupled evanescently into the waveguiding region is coupled out via a second grating 3. The filters 9 serve to filter out scattered light.

The method is preferably used for analysing samples such as egg yolk, blood, serum, plasma or urine.

Another preferred method is obtained in the analysis of samples such as surface water, soil or plant extracts and liquors from biological or synthetic processes.

The present invention relates also to the use of the sensor platform or modified sensor platform according to the invention for the quantitative determination of biochemical substances in affinity sensing.

Since signal generation and detection are limited to the chemical or biochemical recognition surface on the waveguide and disturbance signals from the medium are discriminated, the binding of substances to the immobilised recognition elements can be followed in real time. The use of the method according to the invention in affinity screening or in displacement assays, especially in pharmaceutical product development, by means of the direct determination of association and dissociation rates in a throughflow system at suitable floss rates, is there fore possible also.

The present invention also includes
a) the use of the sensor platform or modified sensor platform according to the invention for the quantitative determination of antibodies or antigens;
b) the use of the sensor platform or of the modified sensor platform for the quantitative determination of receptors or ligands, oligonucleotides, DNA or RNA strands, DNA or RNA analogues, enzymes, enzyme substrates, enzyme cofactors or inhibitors, lectins and carbohydrates, and
c) the use of the sensor platform or modified sensor platform according to the invention for the selective quantitative determination of luminescent constituents of optically opaque fluids.

Optically opaque fluids may be, for example, biological fluids, such as egg yolk, and body fluids, such as blood, serum or plasma, but also environmental analysis samples, such as surface water, dissolved soil extracts or dissolved plant extracts. Also relevant are reaction solutions, such as those obtained, for example, in chemical production, especially dye solutions or reaction solutions of optical brighteners. Also relevant are all types of dispersions and preparations used, for example, in the textiles industry, provided that they comprise one or more luminescent components. The method can thus also be used for quality control.

The following Examples illustrate the invention.

In all of the following Examples, the unit M of concentration denotes mol/l.

EXAMPLES A

Production of Various Sensor Platforms

EXAMPLE A1

Production Using Masks in Vapour Deposition

A polycarbonate (PC) substrate is coated with $TiO_2$ by means of vapour deposition (process: sputtering, deposition rate: 0.5 Å/s, thickness: 150 nm). There is introduced between the target and the substrate, in the immediate vicinity of the substrate, a mask produced from aluminium in which 6 strips 30 mm in length and 0.6 mm in width have been cut. The resulting 6 waveguiding regions (measuring regions) have a trapezoidal profile with a uniform thickness of 150 nm in the central region, which is 600 µm in width, and a layer thickness that decreases at the sides in the form of a gradient (shadowing). Coupled-in laser light is confined in the waveguiding region, since the effective refractive index is highest in the central region, because that region has the greatest layer thickness.

EXAMPLE A2

Production by Subsequent Division

The operation is carried out using an ArF excimer laser at 193 nm. The rectangular laser beam is concentrated using a cylindrical lens to a beam profile 200 µm wide and 20 mm long focused on the sensor platform. The sensor platform has a continuous 100 nm thick layer of $Ta_2O_5$. At an energy density above $1J/cm^2$ the entire layer is ablated with a single laser pulse (10 ns).

EXAMPLE A3

Production by Subsequent Division

The operation is carried out using an Ar-ion laser at 488 nm. The round laser beam is concentrated using a microscope lens (40×) to a diameter of 4 µm focused on the wave-guiding layer. The sensor platform has a continuous 100 nm thick layer of $Ta_2O_5$ and is located on a motor-controlled positioning element (Newport PM500). Under continuous laser irradiation, the platform is driven perpendicular to the beam at 100 mm/s. At an output of 700 mW the entire waveguiding layer is ablated at the focus, with the result that two separate waveguiding regions are formed.

EXAMPLE A 4

Production by the Application of a Structured Absorbing Cover Layer by the Vacuum Method 5 parallel strips of a layer system of chromium/gold are vapour-deposited on the (continuous) metal oxide waveguide consisting of $Ta_2O_5$ (vapour-deposition installation: Balzers BAK 400); first 5 nm of Cr at 0.2 nm/s, then 45 nm of Au at 0.5 nm/s. The coupled-in modes are interrupted at the absorbing layers.

EXAMPLE A5

Production by the Application of a Structured Absorbing Cover Layer by the Aqueous Method The surface of a metal oxide waveguide consisting of $Ta_2O_5$ is silanised with (mercapto-methyl) dimethylethoxysilane in the gas phase at 180° C. With the aid of a fine pipette, colloid solution A (GoldSol supplied by Aurion, average colloid diameter=28.9 nm, concentration: $A_{520} \approx 1$, aqueous solution) is applied to the modified surface in the form of droplets or strips and incubated for 1 hour. After the incubation the surface is washed with water. Guided modal light is absorbed at the incubated sites. Downstream of the incubated sites modal light is no longer present. The same applies in the case of protein A-covered Au colloid solution B (P-9785 supplied by Sigma, average diameter=18.4 nm, $A_{520} \approx 5.5$, in 50% glycerol, 0.15 M NaCl, 10 mM sodium phosphate, pH 7.4, 0.02% PEG 20, 0.02% sodium azide). The absorbing patterns on the waveguide surface are still intact even after flushing several times with water and with ethanol, which demonstrates the stability of the structures produced.

By the manual application of rows of microdrops (1 µl) of colloid solution A, continuous light-absorbing strips can be produced.

EXAMPLE A6

Production by the Application of a Structured Absorbing Cover Layer by the Aqueous Method The surface of a metal oxide waveguide consisting of $TiO_2$ is silanised with (mercapto-methyl) dimethylethoxysilane in the gas phase at 50° C. Then a portion of the waveguide surface in front of and including the second coupling-out grating is incubated for 3 hours with colloid solution B (P-9785 supplied by Sigma, average diameter=18.4 nm, $A_{520} \approx 5.5$, in 50% glycerol, 0.15 M NaCl, 10 mM sodium phosphate, pH 7.4, 0.02% PEG 20, 0.02% sodium azide). The wave propagation at the incubated sites is interrupted completely. The surface of the incubated site is examined using an atomic force microscope and the presence of colloids and the density of the gold particles anchored to the surface that is necessary for the observed light absorption are determined. The average separation of the particles is in the region of approx. 100 nm.

EXAMPLE A7

Production by the Application of a Structured Absorbing Cover Layer by the Aqueous Method The surface of a metal oxide waveguide consisting of $Ta_2O_5$ is silanised with (mercapto-methyl) dimethylethoxysilane (in the gas phase at 180° C.). The waveguide chip is connected to a throughflow cell having parallel, fluidically separate laminar part streams which allow up to five different streams of fluid to be passed in parallel adjacent to one another over the length of the waveguide surface via separate, individually addressable flow openings (1–5). The intention is to produce three waveguiding strips separated by two thinner strips of deposited Au colloids. The throughflow cell is charged at inlets 1, 3 and 5 with buffer (phosphate-buffered sodium chloride solution, pH 7.0) and at inlets 2 and 4 with Au colloid solution. A colloid solution the surface of which is blocked with bovine serum albumin (BSA Gold Tracer supplied by Aurion, average colloid diameter=25 nm, $OD_{520} = 2.0$) is used. The flow rates selected (per channel) are: 0.167 ml/min for the buffer streams 1, 3 and 5 and 0.05 ml/min for the two colloid streams 2 and 4. That results in a width of approx. 1 mm for the colloid stream and approx. 3 mm for the buffer stream. The ratio of colloid stream width to buffer stream width can generally be freely selected via the ratio of the streams.

The streams are applied for 20 min (corresponding to an amount of colloid of 1 ml per channel). After 20 minutes' incubation, the waveguide chip is removed, washed with water and dried with a stream of nitrogen. Guided modal light is completely absorbed by the colloid-immobilised strips and results in three separate light-guiding modes of approx. 3 mm in width.

Application Examples B

EXAMPLE B1

Parallel Detection of Two Different Fluorescein-labelled Oligonucleotides with Complementary Strands Immobilised on Two Physically Separate Regions in a Hybridisation Assay

B1.1 Optical Sensor Platform Having Two Waveguiding Regions, Obtained in Accordance with

EXAMPLE A3

Geometry: 16 mm×48 mm×0.5 mm.

Waveguiding layer: $Ta_2O_5$, n=2.317 at 488 nm, thickness 150±5 nm.

Substrate: Corning Glass C7059, n=1.538 at 488 nm.

Grating: rectangular grating having a modulation depth of 6–7 nm, grating period: 750 nm.

Coupling-in result with excitation at 633 nm

Coupling angle: 4°–5°(second order diffraction)

Coupling-in efficiency: 7% at the site of the grating

Attenuation: 2.5 dB/cm.

B1.2 Optical Design

The excitation light from an argon-ion laser (excitation wavelength 488 nm) is expanded-to 10 mm using a cylindrical lens and directed with the aid of a rotatable mirror from the back of the substrate onto the two gratings of the waveguiding regions. There is pressed onto the top of the waveguiding layer from above, and sealed by an O-ring, a thermostatically controlled throughflow cell having a capacity of approx. 0.07 ml and extending over both waveguiding regions. The luminescences of the two samples, excited in the evanescent field, are recorded simultaneously by two physically separate detectors. The two detectors each consist of a photodiode (SR 1133, Hamamatsu), onto which there are guided by means of an identical glass optical fibre with filtering using an interference filter the luminescences radiated into the cell space. The signals are amplified by means of two transimpedance amplifiers.

The individual elements used for the design are known and are commercially available.

B1.3 Solutions Used

1) Hybridisation buffer (pH 7.75), consisting of 0.069 M phosphate buffer (0.041 M $Na_2HPO_4$+0.028 M $NaH_2PO_4$), 0.176 M KCL, 1 ml of POE-(20)-sorbitol monolaurate (Tween 20, ICI), 1 g of polyacrylic acid PAA 5100, 500 mg/l of sodium azide, made up to 1 litre with distilled water.

2) Sample solution 1 (16*cfl): fluorescein-labelled oligomer, consisting of 16 base pairs (fluorescein-5'-GTTGTGTGGAATTGTG-3' ($10^{-8}$ M) in hybridisation buffer 1), complementary to the oligomer immobilised on the first waveguiding region.

3) Sample solution 2 (15*cfl): fluorescein-labelled oligomer, consisting of 15 base pairs (fluorescein-5'TTTTTCTCTCTCTGT-3' ($10^{-8}$ M) in hybridisation buffer 1), complementary to the oligomer immobilised on the second waveguiding region.

4) Regenerating solution: 50% urea (w/w) in aqueous solution

The solutions are supplied by means of Cavro pumps (10 ml burette volume in each case).

B1.4 Immobilisation Process

Using an oligonucleotide synthesiser (Applied Biosystems 394B), the specific binding partners (3'CAACACACCTTAACAC-5' on the first waveguiding region, 3'AAAAAGAGAGAGAGA on the second waveguiding region) are synthesised directly on the sensor platform silanised with 3-glycidyloxypropyltrimethoxysilane using a method that is standard for oligonucleotide synthesis on particles. However, in contrast to the standard synthesis method, a stable hexaethylene glycol linker is used for anchoring the oligonucleotides to the surface, at the 3' end. The sensor platforms together with the immobilised specific binding partners are washed with water and then used in the assay.

B1.5 Measurement Procedure

Variant 1 of the measurement method (supplying two different analytes, one after the other chronologically, over the two waveguiding regions simultaneously) consists of the following individual steps:

washing for 2 minutes with hybridisation buffer 1) (0.5 ml/min), recording of the background signal;

supplying sample solution 2) for 10 minutes (0.5 ml/min) (after flushing for 5 seconds at 5 ml/min);

flushing for 2 minutes with hybridisation buffer 1);

supplying regenerating solution 4) for 3 minutes (0.5 ml/min);

flushing for 4 minutes with hybridisation buffer 1);

supplying sample solution 3) for 10 minutes (0.5 m/min) (after flushing for 5 seconds at 5 ml/min);

flushing for 2 minutes with hybridisation buffer 1);

supplying regenerating solution 4) for 3 minutes (0.5 ml/min);

flushing for 2 minutes with hybridisation buffer 1).

The isotropically radiated fluorescence from the two waveguiding regions is collected during the procedure by means of lightguide bundles of rectangular inlet cross-section (10 mm*1 mm) positioned directly underneath the sensor platform. The rectangular cross-section of the lightguide bundles is transformed into circular outlets (diameter 6 mm). Immediately downstream of the outlets of the lightguide bundles are similar interference filters (maximum transmission at 530 nm, band width 30 nm). The spectrally filtered fluorescent light is measured by means of two photodiodes. After 10 minutes of supplying fluorescein-labelled 16-mer complementary sample, a fluorescence signal of 42 mV from the first waveguiding region is observed and no signal from the second waveguiding region (1 mV) is observed. In contrast, after 10 minutes of supplying fluorescein-labelled 15-mer complementary sample, a fluorescence signal of 43 mV is measured at the second waveguiding region and no signal (0 mV) is measured at the first waveguiding region. The signal noise is approx. 2 mV.

Variant II of the measurement procedure (supplying two different analytes to the two physically separate waveguiding regions simultaneously using separate cells) consists of the following individual steps:

washing for 2 minutes with hybridisation buffer 1) (0.5 ml/min) in both waveguiding regions, recording the background signals of both channels;

(after flushing for 5 seconds at 5 ml/min) supplying sample solution 2) (0.5 ml/min) to the first waveguiding region and sample solution 3) (0.5 ml/min) to the second waveguiding region for 10 minutes;

flushing both waveguiding regions for 2 minutes with hybridisation buffer 1);

supplying regenerating solution 4) (0.5 ml/min) to both waveguiding regions for 3 minutes;

flushing both waveguiding regions for 4 minutes with hybridisation buffer 1).

The isotropically radiated fluorescence from the two waveguiding regions is collected during the procedure by means of lightguide bundles of rectangular inlet cross-section (10 mm*1 mm) positioned directly underneath the sensor platform. The rectangular cross-section of the lightguide bundles is transformed into circular outlets (diameter 6 mm). Immediately downstream of the outlets of the lightguide bundles are similar interference filters (maximum transmission at 530 nm, band width 30 nm). The spectrally filtered fluorescent light is measured by means of two photodiodes. Clear signals are obtained from both waveguiding regions.

EXAMPLE B2

Detection of Recognition Elements on 5 Parallel Strips

B2.1 Immobilisation of the Recognition Elements

Cy 5.labelled human antibodies, protein A and BSA are immobilised as recognition elements and control molecules in strips on five regions of the sensor platform described in Example A4.

The analyte for all the recognition elements is a Cy 5.5-labelled human antibody that exhibits an affinity reaction with the protein A strips only.

All the strips are 0.6 mm*15 mm. The distance between the strips is 0.6 mm. The strips begin 1 mm to the right of the continuous coupling-in grating.

There is used for the structured immobilisation of recognition elements and control molecules on the surface of the sensor platform a multichannel cell having the following geometry. Six channels having the dimensions: width 0.6 mm* length 15 mm and a depression of the size of the sensor platform used are cut in a teflon right parallelepiped (dimensions: 100 mm*60 mm*18mm). At both ends of the channels, drilled holes are made in the teflon using a 0.6 mm drill, in order to provide access to the individual channels from the underside of the teflon block. As a result of the special shaping of the channels made in the teflon and the selected geometry around the channels, the channels are in the form of 'lips' that project approx. 0.2 mm from the depression cut for the waveguide. The waveguiding layers, the surface of which has previously been chemically modified by means of gas-phase silanisation with 3-mercaptopropyl-dimethylmethoxysilane, are placed in the depression in the multichannel cell in such a manner that the waveguiding layer faces the channels. By pressing the sensor platform against the teflon lips of the multichannel cell, a sealed connection is produced between the surface of the waveguiding regions and the teflon block. The following solutions are injected in to the individual channels via the drilled holes.

Channel 1:1 nM of a solution of a Cy 5.5-labelled human antibody

Channel 2:1 mg/ml of protein A in water

Channel 3:10 mg/ml of BSA in water

Channel 4:1 mg/ml of protein A in water

Channel 5:1 mg/ml of protein A in water

Channel 6: not used

After an incubation period of 2 hours, the channels are washed by injecting demineralised water into the m an d dried by blowing nitrogen through them. The sensor platform is then removed from the multichannel cell and the waveguiding surface is wetted with approx. 400 µl of a BSA solution having a concentration of 10 mg/ml in order to saturate any remaining active binding sites on the silanised surface with a protein (BSA). BSA exhibits no affinity for the Cy 5.5-labelled human antibody used as the analyte in this experiment. After an incubation period of 2 hours, the sensor platform is washed with demineralised water.

B2.2 Experimental Arrangement for the Automatic Fluorescence Measurement of Recognition Elements and Their Binding Partners Immobilised in Strips The measurement arrangement consists of three main components A) Vertically adjustable holding means for the sensor platform with integral throughflow cell for fluid-contacting of the waveguiding regions with different solutions.

B) Optical arrangement having holding means for a laser source and optical elements for the definition of the excitation light beam.

C) Optical arrangement that by means of a lens combination and a mechanical screen projects a strip-shaped region of the waveguide surface onto a detector.

The flow cell is mounted on a computer-controlled translation and rotation unit in such a manner that the coupling-in grating is located exactly on the rotational axis of the rotation unit. Using the translation unit, the flow cell can be positioned, together with the waveguide, along that rotational axis and the mode can thus be coupled in in the region of the five molecule strips immobilised on the waveguide.

The flow cell consists in principle of an aluminium plate having the dimensions: 75 mm*40 mm*5 mm, into the centre of which an O-ring is inset in such a manner that pressing a sensor platform against the O-ring causes a shallow chamber having the dimensions: 28 mm*6 mm*0.2 mm to be formed. For fluid-contacting, the chamber is accessible by way of three holes of 1 mm diameter drilled in the aluminium. Two of those drilled holes, which serve as entrances to the flow cell, are made in the centres of the end faces in the interior of the chamber. When the sensor platform is pressed against the O-ring, the two gratings of the sensor platform are located between those entrances to the flow cell. The third drilled hole serves as an exit from the flow cell and is arranged in such a manner that the coupling-in grating is located symmetrically between one of the entrances and the exit of the flow cell. A buffer is pumped into the cell by way of the entrance at the coupling-in grating and the analyte is pumped into the flow cell by way of the entrance at the coupling-out grating. That construction prevents the coupling-in grating from being contaminated by constituents of the analyte solution (counterflow principle).

A sealing connection between waveguide and flow cell is achieved by means of an O-ring inset into the flow cell. The medium in the flow cell can be replaced by means of hose connections using the counterflow principle.

A diode laser is used to produce a convergent light beam. The laser beam, having a diameter of 0.4 mm, coming from the laser optic forms a constant right angle with the end face of the sensor platform. Using a polariser and a λ/2 plate, the intensity and polarization of the laser beam can be adjusted. A band pass filter having a wavelength of 670 nm eliminates photons that are emitted by the diode laser in the wavelength range of the fluorophores to be detected (690–740 nm) and that would interfere with the fluorescence detection. The angle between the laser beam and the longitudinal axis of the waveguide is freely adjustable using the rotation element and is used to adjust the coupling-in angle for the $TE_0$ mode. The detection optic (C) is focused on the centre of the longitudinal side of the waveguide and at the level of the $TE_0$ mode an d produces on the detector an image of the mode on the waveguide surface. Using a strip screen immediately in front of the detector, only that region that corresponds to the geometry of the molecules immobilised in strips is imaged, i.e. a region of 0.6 mm*15 mm. The detector optic chosen is such that it produces a 1:1 image of the waveguide surface in the plane of the detector. A filter combination substantially eliminates the excitation light and allows virtually only fluorescence photons through to the detector (2*band pass 725 nm).

2.3 Execution of a Multiple Assay

First the flow cell is filled with PBS 7.0 and the coupling-in angle is adjusted using the rotation unit.

The following solutions are pumped in succession through the flow cell per measurement cycle:

1) 1 ml of washing buffer PBS 7.0, flow rate 500 μl/min.
2) 1 ml of analyte—10 pM Cy 5.5-labelled human antibodies, flow rate 250 μl/min.
3) 1 ml of washing buffer PBS 7.0, flow rate 250 μl/min.
4) 1 ml of chaotropic buffer (glycine, pH 2.6), flow rate 250 μl/min.
5) 1 ml of washing buffer PBS 7.0, flow rate 500 μl/min. counterflow: 5 ml of PBS 7.0, flow rate 300 μl/min.

Using computer-controlled multiple valves and piston pumps, the various solutions are pumped through the flow cell in the above sequence and at the above flow rates during the 15 minute measuring cycle.

The vertical position of the flow cell is adjusted at the beginning by means of the translation unit in such a manner that the mode runs exactly in the upper region of the waveguide surface, on which region the Cy 5.5-labelled human antibody has been immobilised beforehand. Since that strip is permanently fluorescent as a result of excitation by the laser beam, the vertical position is adjusted so that the photon counter produces a maximum value. That identifies the position of the immobilised Cy 5.5-labelled human antibody.

Automatic measurement is then started in which by incremental changes in the vertical position of the flow cell by means of the translation unit, which changes correspond to the distance between the immobilised strips, the five strips are moved upwards one after the other in the sequence 1 to 5 in an 8 second rhythm into the focus of the detector. As a result of the geometry described, the $TE_O$ mode is likewise produced only in the selected regions.

While the flow cell, together with the waveguide, is held in one position, the value measured by the photon counter in the selected region in one second is registered as a function of time.

The automatic shuttling between the five different regions of the waveguide is continued throughout the entire 15 minute duration of the measurement. During that period the solutions indicated above are pumped through the measuring cell at the appropriate flow rates. The data obtained can be displayed as a function of time. The region on which the Cy 5.5-labelled human antibody is immobilised (strip/channel 1) fluoresces during the entire measurement cycle and exhibits no interaction with the 10 pM solution of a Cy 5.5-labelled human antibody pumped as analyte into the measuring cell. In the case of regions 2, 4 and 5 of the sensor platform, on which protein A has been immobilised beforehand, an increase in the fluorescence signal to from 4 to 5 times the starting value begins after 150 seconds. The start of the increase correlates with the point in time at which the analyte is pumped into the flow cell. The signal in the case of those channels remains virtually unchanged at a high value, even when after 400 seconds 1 ml of the washing buffer is pumped through the flow cell at a flow rate of 250 μl/min. That behavior is consistent with the specific binding of the labelled antibody to protein A. In region 3 of the sensor platform, BSA has been immobilised beforehand as the control. As expected, that strip/channel exhibits a very low value throughout the measurement, since the Cy 5.5-labelled human antibodies used as analyte react only non-specifically with BSA.

What is claimed is:

1. A sensor platform comprising:
   a continuous substrate; and
   a transparent, planar, inorganic, dielectric waveguiding layer provided on said continuous substrate;
   wherein said waveguiding layer includes a plurality of waveguiding regions, and at least one dividing portion divides said waveguiding layer into said plurality of waveguiding regions;
   wherein said at least one dividing portion has an effective refractive index lower than that of said waveguiding regions or has a material on its surface that absorbs coupled-in light;
   wherein said waveguiding regions are provided with one coupling-in grating each or with a common coupling-in grating for coupling-in of light to said waveguiding regions in such a manner that the direction of propagation of a wave vector of the light is maintained after the coupling-in;
   wherein said plurality of waveguiding regions are formed of the same material;
   wherein said plurality of waveguiding regions are arranged so as to permit light coupled-in to said waveguiding regions to cause evanescent excitation of luminescence or a change of luminescence at each of said plurality of waveguiding regions; and
   wherein, on the surfaces of said waveguiding regions, one or more specific binding partners are immobilized as chemical or biochemical recognition elements for one or more identical or different analytes.

2. A sensor platform of claim 1, wherein
   said waveguiding regions are provided with one coupling-out grating each or with a common coupling-out grating.

3. A sensor platform of claim 1, wherein
   said waveguiding layer is non-polymeric.

4. A sensor platform of claim 1, wherein
   said waveguiding regions are spaced apart from one another.

5. A sensor platform of claim 1, wherein the individual waveguiding regions are arranged to form multiple detection regions.

6. A sensor platform according to claim 5, wherein the individual multiple detection regions are arranged in the form of a rectangular chessboard pattern or in the manner of individual images in a film strip.

7. A modified sensor platform according to claim 1, wherein the specific binding partners on the surface of each waveguiding region are physically separate from one another.

8. A sensor platform according to claim 1, wherein the specific binding partners are antibodies for antigens, binding proteins, such as protein A and G, for immunoglobulins, biological and chemical receptors for ligands, chelators for histidine-tag components, for example histidin-labelled proteins, oligonucleotides and single strands of RNA or DNA for their complementary strands, avidin for biotin, enzymes for enzyme substrates, enzyme cofactors or inhibitors, or lectins for carbohydrates.

9. A sensor platform according to claim 1, wherein an adhesion-promoting layer is located between the waveguiding regions and the immobilized specific binding partners.

10. A sensor platform according to claim 1, wherein the waveguiding regions are arranged in the form of separate strips, rectangles, circles, ellipses or chessboard patterns.

11. A sensor platform according to claim 1, wherein the division into a plurality of waveguiding regions is achieved by means of a change in the effective refractive index between the waveguiding regions and the adjacent material, the difference in effective refractive index being greater than 0.2 units.

12. A sensor platform according to claim 1, wherein the division into a plurality of waveguiding regions is effected by means of an absorbing material on the surface of the waveguiding layer.

13. A sensor platform according to claim 12, wherein the absorbing material is an organic compound.

14. A sensor platform according to claim 12, wherein the absorbing material is a dyed or pigmented polymer.

15. A sensor platform according to claim 1, wherein the substrate is glass, quartz or a transparent thermoplastic plastics material.

16. A sensor platform according to claim 1, wherein the refractive index of the waveguiding regions is greater than 2.

17. A sensor platform according to claim 1, wherein the waveguiding regions are formed of a material containing $TiO_2$, $ZnO$, $Nb_2O_5$, $Ta_2O_5$, $HfO_2$ or $ZrO_2$.

18. A sensor platform according to claim 1, wherein the thickness of the waveguiding regions is from 40 to 300 nm.

19. A sensor platform according to claim 1, wherein the modulation depth of the gratings is from 3 to 60 nm.

20. A sensor platform according to claim 1, wherein the ratio of the modulation depth of the gratings to the thickness of the waveguiding regions is equal to or less than 0.2.

21. A sensor platform according to claim 1, wherein the grating period is from 200 to 1000 nm.

22. A sensor platform according to claim 1, joined with a fluidics disc to form a unit that comprises supply lines and cell spaces.

23. A method for the parallel determination of one or more luminescences using a sensor platform according to claim 1, which method comprises bringing one or more liquid samples into contact with one or more of said waveguiding regions on the sensor platform, coupling excitation light into the waveguiding regions, causing the coupled-in light to pass through the waveguiding regions, thus exciting in parallel in the evanescent field the luminescent substances in the one or more samples or the luminescent substances immobilized on the waveguiding regions and, using optoelectronic components, measuring the luminescences produced thereby.

24. A method according to claim 23, wherein the one or more samples are brought into contact with the waveguiding regions when stationary or are passed over them continuously, the circulation being open or closed.

25. A method according to claim 23, characterized in that in a throughflow system the binding or desorption of luminescence-labelled affinity partners in the evanescent field is followed in real time.

26. A method according to claim 23, wherein (a) either isotropically radiated, evanescently excited luminescences are detected, or (b) wherein evanescently excited luminescences backcoupled into the waveguiding layer are detected via a coupling-out grating or at an edge of the sensor platform, or (c) wherein both the isotropically radiated luminescence and the backcoupled luminescence are detected independently of one another but simultaneously.

27. A method according to claim 23, wherein absorption of the excitation light coupled-in to said waveguiding regions and luminescence at said waveguiding regions is determined simultaneously.

28. A method according to claim 23, wherein the luminescences are excited by various laser light sources of identical or different wavelength.

29. A method according to claim 23 for the quantitative determination of biochemical substances in affinity sensing.

30. A method according to claim 23, wherein the one or more liquid samples comprise egg yolk, blood, serum, plasma or urine, surface water, a soil or plant extract or a liquor from a biological or synthetic process.

31. A method according to claim 23, wherein the one or more liquid samples comprise antibodies or antigens, receptors or ligands, chelators or histidine-tag components, oligonucleotides, DNA or RNA strands, DNA or RNA analogues, enzymes, enzyme substrates, enzyme cofactors or inhibitors, lectins and carbohydrates.

32. A sensor platform of claim 1, wherein
said waveguiding regions are formed on said substrate in such a manner that said sensor platform provides for simultaneous detection of evanescently excited luminescence from one or more analytes.

33. A sensor platform of claim 1, wherein microparticles are attached on the surfaces of the waveguiding regions.

34. A sensor platform of claim 33, wherein said one or more specific binding partners are immobilized on said microparticles.

* * * * *